(12) United States Patent
Ricard et al.

(10) Patent No.: US 9,889,073 B2
(45) Date of Patent: Feb. 13, 2018

(54) COLOUR CHANGING COMPOSITION IN EMULSION FORM COMPRISING A PARTIALLY NEUTRALIZED, CROSSLINKED ACRYLIC HOMOPOLYMER OR COPOLYMER

(71) Applicant: L'OREAL, Paris (FR)

(72) Inventors: Audrey Ricard, La Varenne (FR); Micheline El Achkar, Paris (FR)

(73) Assignee: L'OREAL, Paris (FR)

( * ) Notice: Subject to any disclaimer, the term of this patent is extended or adjusted under 35 U.S.C. 154(b) by 44 days.

(21) Appl. No.: 14/772,989

(22) PCT Filed: Mar. 5, 2014

(86) PCT No.: PCT/IB2014/059454
§ 371 (c)(1),
(2) Date: Sep. 4, 2015

(87) PCT Pub. No.: WO2014/136061
PCT Pub. Date: Sep. 12, 2014

(65) Prior Publication Data
US 2016/0015611 A1    Jan. 21, 2016

(30) Foreign Application Priority Data

Mar. 6, 2013  (EP) ................. 13305255

(51) Int. Cl.
| | | |
|---|---|---|
| *A61K 8/11* | (2006.01) | |
| *A61K 8/81* | (2006.01) | |
| *A61K 8/06* | (2006.01) | |
| *A61K 8/37* | (2006.01) | |
| *A61K 8/73* | (2006.01) | |
| *A61K 8/19* | (2006.01) | |
| *A61K 8/02* | (2006.01) | |
| *A61K 8/29* | (2006.01) | |
| *A61K 8/55* | (2006.01) | |
| *A61Q 1/02* | (2006.01) | |
| *A61K 8/34* | (2006.01) | |
| *A61Q 19/00* | (2006.01) | |

(52) U.S. Cl.
CPC .............. *A61K 8/11* (2013.01); *A61K 8/0245* (2013.01); *A61K 8/062* (2013.01); *A61K 8/19* (2013.01); *A61K 8/29* (2013.01); *A61K 8/345* (2013.01); *A61K 8/375* (2013.01); *A61K 8/553* (2013.01); *A61K 8/732* (2013.01); *A61K 8/8147* (2013.01); *A61K 8/8158* (2013.01); *A61Q 1/02* (2013.01); *A61Q 19/00* (2013.01); *A61K 2800/10* (2013.01); *A61K 2800/26* (2013.01); *A61K 2800/412* (2013.01); *A61K 2800/43* (2013.01); *A61K 2800/56* (2013.01); *A61K 2800/58* (2013.01); *A61K 2800/594* (2013.01); *A61K 2800/652* (2013.01); *A61K 2800/654* (2013.01)

(58) Field of Classification Search
CPC ........ A61K 8/0245; A61K 8/062; A61K 8/11; A61K 8/19; A61K 8/29; A61K 8/345; A61K 8/375; A61K 8/553; A61K 8/732; A61K 8/8147; A61K 8/8158; A61K 2800/10; A61K 2800/26; A61K 2800/412; A61K 2800/43; A61K 2800/56; A61K 2800/58; A61K 2800/594; A61K 2800/652; A61K 2800/654; A61Q 1/02; A61Q 19/00

See application file for complete search history.

(56) References Cited

U.S. PATENT DOCUMENTS

| | | |
|---|---|---|
| 4,756,906 A | 7/1988 | Sweeny |
| 2007/0092457 A1 | 4/2007 | Librizzi et al. |
| 2011/0034408 A1* | 2/2011 | Lorant ............. A61K 8/8158 514/54 |
| 2012/0178662 A1 | 7/2012 | Lachmann et al. |
| 2012/0183479 A1 | 7/2012 | Loeffler et al. |
| 2014/0341987 A1 | 11/2014 | Chai et al. |
| 2014/0356402 A1 | 12/2014 | Lemoine et al. |
| 2014/0356403 A1 | 12/2014 | Zhu et al. |

FOREIGN PATENT DOCUMENTS

| | | |
|---|---|---|
| CN | 101795729 A | 8/2010 |
| EP | 1 776 985 A2 | 4/2007 |
| EP | 1 776 985 A3 | 4/2007 |
| EP | 2 277 982 A1 | 1/2011 |
| FR | 2 591 102 A1 | 6/1987 |
| JP | 2011-79804 A | 4/2011 |
| WO | WO 2009/022306 A2 | 2/2009 |

OTHER PUBLICATIONS

Neumann et al SOFW-Journal 125, 6, 8-10, 1999.*
U.S. Appl. No. 14/372,862, filed Jul. 17, 2014, 2014/0356402 A1, Cyril Lemoine, et al.
U.S. Appl. No. 14/372,872, filed Jul. 17, 2014, 2014/0356403 A1, Rong Zhu, et al.
U.S. Appl. No. 14/372,888, filed Jul. 17, 2014, 2014/0341987 A1, Yihao Chai, et al.
International Search Report and Written Opinion of the International Searching Authority dated Oct. 30, 2014, in PCT/IB2014/059454, filed Mar. 5, 2014.
European Search Report dated Aug. 6, 2013, in Patent Application No. EP 13 30 5255, filed Mar. 6, 2013.
U.S. Appl. No. 14/772,929, filed Sep. 4, 2015, Ricard, et al.
Notification of the First Office Action dated Nov. 20, 2016 in Chinese Patent Application No. 201480012561.1 with English translation.

* cited by examiner

*Primary Examiner* — Suzanne Ziska
*Assistant Examiner* — Thurman Wheeler
(74) *Attorney, Agent, or Firm* — Oblon, McClelland, Maier & Neustadt, L.L.P.

(57) ABSTRACT

The instant invention relates to a color changing composition in the form of an emulsion comprising, at least: a) microcapsules containing releasable colorant(s), said microcapsules comprising: —a core comprising one organic material, —at least one layered coating surrounding said core, the layered coating comprising at least one polymer, at least one colorant, and advantageously at least one lipid-based material, b) at least partially neutralized, crosslinked acrylic homopolymers or copolymers preferably in a non-particulate form.

15 Claims, 1 Drawing Sheet

COLOUR CHANGING COMPOSITION IN EMULSION FORM COMPRISING A PARTIALLY NEUTRALIZED, CROSSLINKED ACRYLIC HOMOPOLYMER OR COPOLYMER

The present invention relates to a color-changing composition in the form of an emulsion comprising a specific stabilizing system in particular useful for care, hygiene and/or makeup of keratin materials.

In particular, a color-changing composition according to the invention may be any type of cosmetic composition such as a foundation, a lip balm, a lip gloss, an eyeliner, a mascara, a body makeup product, a skin colouring product, a care product such as a care cream, a 'BB' product (Blemish Balm product able to cover imperfections), a tinted cream or an antisun product, preferably a foundation or BB product. The color-changing composition according to the invention may be liquid or solid, in particular liquid.

A composition of the invention is especially a composition intended to be applied to a keratin material, in particular the skin and more particularly facial skin.

Cosmetic compositions, especially foundations, are commonly used to give the skin an aesthetic colour, but also to hide skin imperfections such as redness and/or marks. In this regard, many formulations have been developed to date.

In this respect, there is a growing interest in cosmetic products that provide a change in color in response to external incentives such for example shear force.

Generally, this purpose is achieved by including in cosmetic composition microencapsulated colorants wherein, upon application on the skin, the composition provides the expected changing color. More particularly, the change of color is provided by the colorant-containing microcapsules, which upon rupture by application of a mechanical force, release the entrapped colorant into the composition, thereby changing its color. A mechanical action such as rubbing spread the topical composition and facilitates its penetration into the skin. The immediate change of color of the composition provides a visual esthetical effect.

Different types of entrapped colorants and more particularly pigments-containing microcapsules are already available. They mainly differ through the type of entrapping material(s) and/or the type of encapsulation.

The instant invention is more particularly concerned with microcapsules containing releasable colorant(s), said microcapsules comprising:
  a core comprising one organic material,
  at least one layered coating surrounding said core, and comprising at least one polymer, at least one colorant, and advantageously at least one lipid-based material.

Such microcapsules containing releasable colorant(s) are particularly interesting since they mask the original color of the encapsulated colorants, increase the stability of these colorants against degradation, and prevent undesirable release of the encapsulated colorants into the composition during the manufacturing process and prolonged storage.

However, colorant-containing microcapsules are not always stable in any media.

With some colorant-containing microcapsules it may be difficult to permanently retain the colorant over long periods of time and when subjected to different environments and conditions. This is true of pigments, oil soluble dyes, and water soluble dyes. Thus, such microcapsules may gradually release the colorant, or "bleed", over time when tested for prolonged periods at elevated temperatures. This release phenomenon may more particularly take place when the microparticules are kept in an emulsion medium and more particularly in an Oil-in-Water type emulsion. Color bleed occurs when a dye or pigment migrates through or off of microspheres/microcapsules through contact with moisture and/or other ingredients in a formulation such as alcohols or glycols, surfactants, silicones, oils, preservatives, salts and other components typically found in cosmetic formulations. Leeching or bleed of the colorant in cosmetic composition can impair the long term visual effect of the cosmetic both in the container and on the substrate.

As far as emulsions are concerned, and in particular O/W emulsions, it remains a need to provide compositions wherein the microcapsule stability is optimal. Particularly it remains a need to have at disposal emulsions, and in particular O/W emulsions, which are notably stable over long period of time and when subjected to changing conditions like changing temperature or pressure.

Indeed some constituents, particularly some surfactants presenting the property of stabilising emulsions may provoke destabilisation of the microcapsules.

In this case, rupture of the microcapsules spontaneously occurs in the bulk of the emulsion without that any rubbing or pressing force has been applied. This rupture of the microcapsules often results from a softening of the external layer and leads to a release of the color e.g. pigments in the emulsion bulk.

As a consequence the bulk appearance becomes dirty grey, and messed up if those kinds of breakable microcapsules are introduced in formula. The release of the microcapsules leads to visible effects like emergence of colored bead in the white bulk and also coloration of the bulk.

Then it remains a need to have emulsions and in particular O/W emulsions which remain stable when brought to changing temperatures that is cold country temperatures and hot country temperatures.

Particularly it remains a need to dispose of emulsions which remain stable over a prolonged time e.g. during 2 months at room temperature and even at 37° C. or 45° C.

It remains a need to have emulsions, in particular O/W emulsions wherein the number of microcapsules which break, without applying a force able to achieve this rupture of the microcapsules, during the storage is very low that means less than 5%. The force able to achieve the microcapsule rupture is the minimal conventional force necessary for applying or spreading a cosmetic composition on the skin.

It also remains a need to propose a composition with caring appearance which provides good makeup effects, particularly a good covering effect.

Based on this, lots of cosmetic companies focus on looking for some pigments encapsulating technologies, aiming to get clear and clean bulk tone, but still delivering proper makeup results in particular a final glowing and natural look.

Thus there is a need of colorant-containing microcapsules, which capsules retain good shatter resistance and exhibit improved bleed resistance.

There is also a need to provide a cosmetic composition which allows the preferred colouration or gradation pattern to be adjusted by varying the method or intensity of application onto the skin or the use of microcapsules containing different colorants.

There is also a need to provide a cosmetic composition stable with a large panel of solvent/ingredient associated.

There is also a need to provide a cosmetic composition wherein the microcapsules are or are not visible inside the bulk of the composition depending on the desired appearance.

There is also a need for a cosmetic composition containing pigment-encapsulated microcapsules which do not provoke to the user a discomfort feeling when applied.

There is also a need to provide a cosmetic composition containing pigment-encapsulated microcapsules which disintegrate rapidly indeed immediately when applied, with a liquid feeling on the skin and leading to coloured compositions devoid of any granular aspect. Particularly, the composition may present different shades or color gradations depending on the rubbing strength.

There is also a need to provide pigment-encapsulated microcapsules with a hardness sufficient to be compounded in an industrial process without alteration. Advantageously the hardness of the microcapsules does not significantly decrease during the preparation process.

In particular, the technical problem underlying the present invention that is obtaining emulsions and in particular Oil-in-Water emulsions, comprising microcapsules containing releasable colorant(s), has been solved by using a specific stabilizing system.

Surprisingly and advantageously, the compositions according to the invention meet the needs of the prior art.

Thus, according to one of its aspects, a subject of the invention is a changing-colour composition for caring for and/or making up keratin materials on the form of an emulsion comprising, at least:
a) microcapsules containing releasable colorant(s), said microcapsules comprising:
  a core comprising one organic material,
  at least one layered coating surrounding said core, the layered coating comprising at least one polymer, at least one colorant, and advantageously at least one lipid-based material,
b) at least partially neutralized, crosslinked acrylic homopolymers or copolymers, preferably in a non-particulate form.

The at least partially neutralized, crosslinked acrylic homopolymer or copolymer is preferably present in the composition in a non-particulate form.

The composition comprises a physiologically acceptable medium comprising an aqueous phase and a fatty phase.

The emulsion is a Water/Oil emulsion or an Oil/Water emulsion and preferably an Oil/Water emulsion.

In another preferred embodiment, the composition comprises at least one 2-acrylamido-2-methylpropanesulphonic acid polymer, preferably a 2-acrylamido-2-methylpropanesulphonic acid homopolymer.

The microcapsules used according to the present invention are breakable upon spreading of the emulsion over the skin. The rubbing or pressing of the emulsion on the skin allows the release of the microcapsule content.

The emulsions according to the present invention are notably stable, particularly during 2 months at room temperature and even at 37° C. or 45° C. and they present optimal cosmetic properties. Indeed the emulsions according to the present invention present an appropriate fluidity: they are easy to handle and further easy to apply and to spread on the skin. Furthermore, the inventors noticed that the emulsions according to the invention stay without any color release.

These emulsions also present a required texture for a cosmetic use: they are not sticky, soft to the touch and the texture is rebounded.

Generally, the microcapsules used according to the invention have average particle sizes of up to about 800 µm in diameter. Preferably the average particle size is less than about 400 µm in diameter of the colorant microcapsules for skin care applications. Preferably, the average particle size will be from 10 µm to 800 µm, advantageously from 40 µm to 800 µm, in particular from 50 µm to 600 µm, in particular from 50 µm to 400 µm in diameter.

According to a preferred embodiment, the average particle size is in the range of about 40 µm to 400 µm in diameter, preferably of about 50 µm to 300 µm in diameter, in particular from 60 µm to 250 µm in diameter and more preferably of about 80 µm to 200 µm in diameter.

Preferably the microcapsules containing releasable colorant(s) are multi-layered microcapsules Preferably the microcapsules containing releasable colorant(s) are multi-layered microcapsules containing releasable colorant(s), said microcapsules comprising:
  an uncoloured core consisting in one organic material, and
  a multi-layered coating surrounding said core and comprising at least one organic inner layer and one organic outer layer of different colour and entrapping respectively at least one colorant.

Preferably, the microcapsules comprise at least two layers preferably at least one organic colored inner layer and one organic outer layer of different colour.

Preferably, the core comprises at least one monosaccharide or its derivatives as said organic material, in particular a monosaccharide-polyol advantageously selected from mannitol, erythritol, xylitol, sorbitol and mixtures thereof, preferably mannitol.

Advantageously, the layered coating surrounding said core comprises at least one hydrophilic polymer(s) selected from the group consisting of polysaccharides and derivatives, preferably the ones including one type of ose or several type of ose(s), preferably several type of ose(s) including at least D-glucose units, in particular starch and derivatives, cellulose or derivatives, and more preferably starch and derivatives.

Preferably, the microcapsules include at least one lipid based material, preferably with amphiphilic properties such as lecithins and in particular hydrogenated lecithin.

Advantageously the core represents from 1% to 50% by weight, preferably 5 to 30% by weight, and in particular from 10 to 20% by weight relative to the total weight of the microcapsule.

Advantageously, the colorant(s) represent from 20% to 90%, preferably from 30% to 80%; in particular from 50% to 75% by weight relative to the microcapsule.

Particularly the microcapsules comprises at least:
  a inner core made of monosaccharide-polyol, preferably mannitol,
  at least two layers of different colour,
  at least one hydrophilic polymer preferably selected from polysaccharide or derivatives, and more preferably from starch or derivatives,
  and advantageously at least one lipid based material, preferably an amphiphilic compound, more preferably a phospholipid, even more preferably phosphoacylglycerol such as hydrogenated lecithin.

Preferably the microcapsules containing releasable colorant(s) are multi-layered microcapsules containing releasable colorant(s), said microcapsules comprising:
  an uncoloured core consisting in one organic material, and
  a multi-layered coating surrounding said core and comprising at least one organic inner layer and one organic outer layer of different colour and entrapping respectively at least one colorant.

According to an embodiment, each layer from the microcapsule contains at least one specific colorant or a specific blend of colorant(s).

According to another embodiment, the outer layer from the microcapsule contains at least one specific colorant or a specific blend of colorant(s).

Particularly the colorants are pigments, preferably selected from the group consisting of metallic oxides.

According to an embodiment, one layer from the microcapsule contains iron oxides and titanium dioxide ($TiO_2$) as colorants.

According to an embodiment, one layer from the microcapsule only contains titanium dioxide ($TiO_2$) as colorant.

The composition may comprise at least 0.1% to 20% by weight, preferably between 0.5% and 15% by weight and in particular between 2 and 10% by weight of microcapsules based on weight of the composition.

The composition according to the invention may further comprises from 0.1 to 70% by weight relative to the weight of the composition, of additional cosmetic ingredient(s) selected from volatile and non-volatile silicon or hydrocarbon oils, surfactants, fillers, additional gelifying agents, thickening agents, film forming agents, polymers, preservatives, silicone elastomer, self-tanning agents, additional non-entrapped colorants, cosmetic actives, pH regulators, perfumes, UV filters and mixtures thereof.

The composition according to the invention, which is preferably a makeup foundation, provides a strong moisturizing sensation, creamy texture with very comfortable feeling during application, and sheer natural makeup result after application. At the end, all these features help to deliver a very good balance of skincare efficacy perception (creamy and, moisturization) as well as makeup efficacy (proper coverage and natural radiance). Moreover the composition according to the invention may present a sunscreen effect.

Advantageously the microcapsules are deformable in the presence of the aqueous phase.

Advantageously the microcapsules inside the composition are breakable under pressure at the application on the keratinic materials.

The present invention is also directed to a cosmetic process for caring for and/or making up keratinic materials, comprising application on said keratinic materials in particular on the skin of a composition according to the invention.

The term "physiologically acceptable medium" is intended to denote a medium that is particularly suitable for applying a product of the invention to keratin materials, especially the skin and more particularly facial skin.

The word "capsule" is also used to mention "microcapsule".

The "physiologically acceptable medium" comprises the aqueous phase used according to the present invention.

For the purposes of the present invention, the term "keratin material" is intended to cover the skin, mucous membranes such as the lips, the nails and the eyelashes. The skin and the lips, in particular facial skin, are most particularly considered according to the invention.

As emerges from the examples that follow, compositions in accordance with the invention prove to be advantageous in several aspects.

Encapsulation of the colorants prevents undesirable re-agglomeration of pigments during manufacture and prolonged storage of the cosmetic compositions.

As the microcapsules of the invention have the ability of swelling or softening in contact of an aqueous phase as defined hereunder, they are advantageously deformable when applied on a keratin material and consequently provide a soft feeling to the user. Furthermore, their low size contributes to not create any discomfort or unfavourable, grainy, feeling when applied.

However, the microcapsules of the invention are soft enough to rupture upon very slight rubbing or pressing on the skin in order to release their content but, nevertheless, are durable enough to avoid destruction of the coating during manufacture, even during an industrial process, and storage of corresponding change-color composition.

In addition, the microcapsule of the invention allows the use of regular equipment for the preparation of the compositions of the invention because no coloring of the apparatus occurs during the manufacturing process.

Accordingly, the microcapsules of the present invention are particularly interesting since they mask the original color of the encapsulated colorants, increase the stability of these colorants against degradation, and prevent undesirable release of the encapsulated colorants into the composition during the manufacturing process and prolonged storage.

At last, compositions of the invention also have the advantage of satisfying a consumer expectation in terms of cosmetic products.

According to another of its aspects, a subject of the present invention is also directed to a cosmetic process comprising at least the steps consisting in applying at least part of a composition according to the invention on the surface of a keratin material, in particular the skin.

According to the invention, the "color changing composition" means a composition wherein the color before application is different from the color after application, this difference being visible to the naked eyes.

In particular, this color changing composition may be linked to a color-difference ΔE in CIE Lab system 1976 (ΔE before/after application) value.

The ΔE is defined by the equation:

$$\Delta E^* = \sqrt{((L_1-L_2)^2+(a_1-a_2)^2+(b_1-b_2)^2}:$$

wherein $L_1$, $a_1$, $b_1$ are the parameters in the colorimetric space of the 1st color (composition before application) and $L_2$, $a_2$, $b_2$ the ones for the $2^{nd}$ color (composition after the application and homogenization on the keratinic material). These values may be measured by spectrophotometer or with a Chrosmasphere (for composition applied on skin).

The color changing composition according to the invention may be characterized as having a ΔE before/after application superior to 1, in particular superior or equal to 2, preferably superior or equal to 3.

Microcapsules Containing Releasable Colorant(s)

The term "microcapsule", as used herein, refers to a spherical microcapsule containing at least one layered coating entrapping at least one colorant and surrounding a core chemically different from the coating. Microcapsules are distinct from microspheres, which consist of spherical homogeneous matrix.

According to an embodiment, the "at least one layered coating" is a multi-layered coating preferably an organic multi-layered coating.

The term "multi-layer microcapsule" refers to a microcapsule consisting of a core surrounded by a coating based on one or more inner layer(s) and one outer layer. The one or more inner layer(s) forming the multi-layer coating of the multi-layer microcapsule and the single outer layer of the microcapsule may be formed of the same or different wall-forming organic compound(s).

The microcapsule according to the invention comprises a core also called "inner core" surrounded by a coating based on one or more layer(s). In a preferred embodiment, the microcapsule is a 'multi-layers' microcapsule, comprising at least one inner layer and one outer layer. The one or more inner layer(s) forming the multi-layer coating of the multi-layer microcapsule and the single outer layer of the microcapsule may be formed of the same or different wall-forming organic compound(s).

In a particular embodiment the inner layer and the outer layer are formed of the same wall forming organic compounds, the core is then surrounded by a one layer coating.

In one embodiment, the outer layer does not comprise any colorant. In another embodiment, the outer layer comprises at least one colorant.

The term "wall-forming organic compound" refers to an organic compound or a combination of two or more different organic compounds as defined herein, which form a component of the layer(s) of the microcapsules. In a preferred embodiment, the 'wall-forming organic compound' comprises at least one polymer.

The term "colorant" refers to organic pigments such as synthetic or natural dyes selected from any of the well known FD&C or D&C dyes, inorganic pigments such as metal oxides, or lakes and any combination (blend) thereof. Accordingly, the colorant useful according to the present invention may be oil-soluble or oil-dispersible or with limited solubility in water.

In preferred embodiments, the colorant is an inorganic pigment, more preferably a metal oxide.

In particular, the average particle size may be from 50 to 1000 Mesh (around 400 µm to 10 µm), in particular from 60 to 200 Mesh (around 250 µm to 75 µm) as measured by the sieving test method or observed by microscope.

Preferably, a composition according to the invention may comprise from 0.1% to 20% by weight and preferably from 0.5% to 15% by weight of microcapsules relative to the total weight of the said composition.

In particular for a skin care composition according to the invention, the amount of microcapsules will range from 0.1% to 5%, preferably from 0.2% to 3% by weight relative to the total weight of composition.

In particular for a make-up composition according to the invention, the amount of microcapsules will range from 0.5% to 20%, preferably from 1% to 15%, more preferably from 2% to 10% by weight relative to the total weight of composition.

According to a particular embodiment, the encapsulated colorant(s) may be present in a composition according to the invention in an amount in active matter of encapsulated pigments ranging from 0.5% to 20% by weight, in particular from 1% to 15% by weight, and more particularly from 2% to 12% by weight, of the total weight of said composition.

The microcapsules will be integrated in the cosmetic formula generally at the latest stages of the formulation and after filtering stages if any, to avoid the microcapsules being broken. Preferably, the microcapsules according to the inventions are added and mixed uniformly at temperatures under 50° C. They are mixed gently with a paddle rather than a homogenizer.

The microcapsules may be produced by several methods known to the man skilled in the art within the coating or encapsulation domain, including pelletization, granulation, coating, etc. For example, the microcapsules may be obtained by a method comprising mixture of the compounds (actives, pigments, polymers, solvents) and drying to form capsules as disclosed in WO01/35933 and WO2011/027960, or a method comprising granulation and coating by spray drying as disclosed in FR2841155, or by fluidized bed technology, which has been used in the food and pharmaceutical industry for a long time for coating and encapsulating ingredients. As an example may be cited WO2008/139053, which concerns the preparation of spheroid multilayer capsules comprising a core of sugar and concentric layers of pharmaceutical actives. Fixation of pharmaceutical actives on the core is achieved by impregnation, pulverization or projection, and then the $1^{st}$ layer is dried before application of a second one.

Fluid bed process is disclosed for example in Teunou et al. (Fluid-Bed Coating, Poncelet, 2005, D. *Food Science and Technology* (Boca Raton, Fla., United States), Volume 146 Issue Encapsulated and Powdered Foods, Pages 197-212). A specific feature of the fluid bed process is that it leads to coated particles wherein the core is well encapsulated, compared to spray drying, which leads to a matrix with the core material randomly dispersed in a polymer.

In a preferred embodiment, the microcapsules are obtained by fluid bed process.

According to this embodiment, preferably at least one layer of the microcapsules is obtained by fluid bed process.

In a particular embodiment, the outer layer is obtained by fluid bed process.

In another particular embodiment at least one inner layer is obtained by fluid process.

Most preferably, all layers are obtained by fluid bed process.

A man skilled in the art knows how to adjust air quantity, liquid quantity and temperature allowing to reproduce a capsule according to the invention.

Preferably a fluid bed process implemented according to the invention includes Würster process and/or tangential spray process. Such a process allows, contrary to a pelletization process, to prepare spherical capsules with a core surrounded by one or more circumferential layers.

When the whole process for preparing the layers surrounding the core of the microcapsules according to the invention is carried out by fluid bed process, the microcapsule layers are advantageously regular, concentric and present a homogenous thickness.

Different examples of preparation of capsules according to the invention will be given later in this description.

I a) Core

The core is made of at least an organic material. The size of said core preferably ranges from 500 nm to 150 µm in diameter.

Preferably the core is in a solid and/or crystal form at room temperature.

In a particular embodiment, the organic material is selected from organic materials having high water dissolvability. Preferably, the core is water-soluble or water-dispersible.

In a particular embodiment, the core is uncoloured, i.e. it does not contain colorant material.

In a particular embodiment, the core is based on only one compound. This compound is organic and more preferably is a natural compound.

According to a preferred embodiment, the core is sugar-alcohol, preferably a monosaccharide-polyol advantageously selected from mannitol, erythritol, xylitol, sorbitol.

In a particular embodiment, the core is made of mannitol and more preferably exclusively made of mannitol.

According to an alternative embodiment, the core contains at least mannitol and at least one additional ingredient being preferably a polymer selected from hydrophilic polymers. In particular, such a core may comprise mannitol and hydrophilic polymers chosen among cellulose polymers, starch polymers and their mixture, preferably their mixture.

In a preferred embodiment, the cellulose polymer is a carboxymethylcellulose and the starch polymer is a non-modified natural starch, for example corn starch.

The core may be constituted by a seed (or crystal) of one of the previous materials.

The core is preferably contained in an amount of from 1% to 50% by weight, preferably 4 to 40% by weight, in particular 5 to 30% by weight, and in particular from 10 to 20% by weight with respect to the total weight of the micro capsule.

The mannitol is preferably contained in an amount of from 2% to 100% by weight, preferably 5 to 100% by weight, and in particular 100% by weight with respect to the total weight of the core.

The mannitol is preferably contained in an amount of from 1% to 50% by weight, preferably 4% to 40% by weight, in particular 5% to 30% by weight, and in particular from 10% to 20% by weight with respect to the total weight of the microcapsule.

I b) External Layer(s) or Coating

As disclosed previously, the core is advantageously surrounded with a coating, or external layer(s) preferably comprising at least one inner layer and one outer layer. In this latter case, these layers preferably extend concentrically in respect with the core.

The layer(s) is/are preferably organic, i.e. contain(s) at least one organic compound as wall-forming material. Preferably, the inner and/or outer layer(s) include(s) at least one polymer, and in particular a hydrophilic polymer.

Polymer(s)

Preferably, the microcapsule according to the invention, and in particular the external layer(s) comprise(s) hydrophilic polymers selected from the group consisting of polysaccharides and derivatives, acrylic or methacrylic acid homopolymers or copolymers or salts and esters thereof, and their mixture.

In a preferred embodiment, the microcapsule according to the invention, and in particular the external layer(s) comprise(s) hydrophilic polymers selected from the group consisting of polysaccharides and derivatives, and in particular starch polymers.

The said polymer(s) is (are) advantageously selected from (poly)(alkyl)(meth)acrylic acid and derivatives, notably (poly)(alkyl)(meth)acrylate and derivatives, preferably from alkylacrylic/alkylmethacrylic acid copolymers and their derivatives, and most preferably is a copolymer of ethyl acrylate, methyl methacrylate and low content of methacrylic acid ester with quaternary ammonium groups provided under the tradename of EUDRAGIT RSPO from Evonik Degussa.

Said polysaccharides and derivatives are preferably selected from chitosan polymers, chitin polymers, cellulose polymers, starch polymers, galactomannans, alginates, carrageenans, mucopolysaccharides, and their derivatives, and the mixture thereof.

In a preferred embodiment, the external layer(s) is/are devoid of microcrystalline cellulose.

According to one particularly preferred embodiment, said polysaccharides and their derivatives are preferably selected from the ones including one type of ose or several type of ose(s), preferably several types of oses, in particular at least D-Glucose unit(s) as ose(s), preferably starch polymers, cellulose polymers, and derivatives, and the mixture thereof.

According to a preferred embodiment, the microcapsule contains at least one hydrophilic polymer selected from the group consisting of starch and its derivatives, in particular corn starch, cellulose and its derivatives, homo- and/or co-polymer of methacrylic acid and/or methacrylic acid ester or co-polymer of (alkyl)acrylic acid and/or (alkyl) methacrylic acid and their derivatives, preferably their salts and their ester, and in particular the capsule contains polymethyl methacrylate.

According to a preferred embodiment, the microcapsule contains at least one hydrophilic polymer selected from the group consisting of starch and its derivatives, in particular corn starch.

Starch usable according to the present invention is usually issued from vegetable raw materials, such as rice, soybeans, potatoes, or corn. Starch can be unmodified or (by analogy with cellulose) modified starch. In a preferred embodiment, the starch is unmodified.

Preferred homo- and/or co-polymer of methacrylic acid and/or methacrylic acid ester are those wherein the copolymer of methyl methacrylate and ethyl acrylate has a molecular weight from 750 to 850 kDa.

Cellulose derivatives include, for example, alkali celluloses carboxymethyl cellulose (CMC), cellulose esters and ethers, and aminocelluloses. In a particular embodiment, the cellulose is a carboxymethyl cellulose (CMC).

According to a preferred embodiment, the capsule contains at least starch derivative, in particular corn starch, polymethyl methacrylate, co-polymer of (alkyl)acrylic acid and/or (alkyl)methacrylic acid and their derivatives preferably their salts and their ester, and/or cellulose derivative.

Preferably, the microcapsule contains polymer(s) which are not cross-linked.

The polymer(s) may be in one or several layer(s).

In another embodiment, the polymer(s) may be in the core.

The microcapsule may contain polymer(s) in the core and/or in the layer(s).

In a particular embodiment, the polymer(s) is (are) in the core and in the layer(s).

In an embodiment, the core contains at least starch and/or cellulose derivative as polymer(s). When the starch is contained within the core, it represents the main ingredient of such a core, i.e. the weight amount of starch is greater than the respective amount of other compounds of the core.

The polymer may represent from 0.5 to 20% by weight of the microcapsule, in particular from 1 to 10% by weight, preferably from 2 to 8% by weight of the microcapsule.

The different layers forming the coating may be based on identical or different polymers. Advantageously, they will be formed from the same polymer.

In contrast, the layers will be advantageously differently coloured.

This different colour may be obtained through the use of different colorants but also the use of different concentrations in at least one colorant when the colorant will be the same for two layers.

In a particular embodiment, the outer layer contains at least one colorant.

In another embodiment, the outer layer does not contain any colorant.

Colorant(s)

As previously stated, "colorant" includes any organic or inorganic pigment or colorant approved for use in cosmetics by CTFA and the FDA used in cosmetic formulations.

Thus the term "colorant" refers to organic pigments such as synthetic or natural dyes selected from any of the well known FD&C or D&C dyes, to inorganic pigments such as metal oxides, or lakes such as the ones based on cochineal carmine, barium, strontium, calcium or aluminum and any combination (blend) thereof. Such colorants are detailed here-after.

In a particular embodiment, the colorant may be water-soluble or water-dispersible.

In another embodiment, the colorant useful according to the present invention may be oil-soluble or oil-dispersible or with limited solubility in water.

In preferred embodiments, the colorant is an inorganic pigment, more preferably a metal oxide.

Advantageously, the colorants of the multi-layer microcapsules are primary metal oxides selected from iron oxides, titanium dioxide, aluminum oxide, zirconium oxides, cobalt oxides, cerium oxides, nickel oxides, tin oxide or zinc oxide, or composite oxides, more preferably an iron oxide selected from red iron oxide, yellow iron oxide or black iron oxide, or a mixture thereof.

The layer(s) may also contain lakes corresponding to an organic colorant secured to a substrate. Such (a) lake(s) is (are) advantageously chosen among the here-below material, and their mixture(s):
carmin of cochineal;
organic pigments of azoic, anthraquinonic, indigoid, xanthenic, pyrenic, quinolinic, triphenylmethane, fluoran colorants; Among the organic pigments may be cited those known under the following trademark references: D&C Blue n° 4, D&C Brown n° 1, D&C Green n° 5, D&C Green n° 6, D&C Orange n° 4, D&C Orange n° 5, D&C Orange n° 10, D&C Orange n° 11, D&C Red n° 6, D&C Red n° 7, D&C Red n° 17, D&C Red n° 21, D&C Red n° 22, D&C Red n° 27, D&C Red n° 28, D&C Red n° 30, D&C Red n° 31, D&C Red n° 33, D&C Red n° 34, D&C Red n° 36, D&C Violet n° 2, D&C Yellow n° 7, D&C Yellow n° 8, D&C Yellow n° 10, D&C Yellow n° 11, FD&C Blue n° 1, FD&C Green n° 3, FD&C Red n° 40, FD&C Yellow n° 5, FD&C Yellow n° 6;
the water-insoluble salts of sodium, potassium, calcium, baryum, aluminum, zirconium, strontium, titanium, of acid colorants such as azoic, anthraquinonic, indigoids, xanthenic, pyrenic, quinolinic, triphenylmethane, fluoran colorants, these colorants may include at least one carboxylic or sulfonic acid group.
The organic lakes may also be protected by an organic support such as rosin or aluminum benzoate.

Among the organic lakes, we may in particular cite those known under the following names: D&C Red n° 2 Aluminum lake, D&C Red n° 3 Aluminum lake, D&C Red n° 4 Aluminum lake, D&C Red n° 6 Aluminum lake, D&C Red n° 6 Barium lake, D&C Red n° 6 Barium/Strontium lake, D&C Red n° 6 Strontium lake, D&C Red n° 6 Potassium lake, D&C Red n° 6 Sodium lake, D&C Red n° 7 Aluminum lake, D&C Red n° 7 Barium lake, D&C Red n° 7 Calcium lake, D&C Red n° 7 Calcium/Strontium lake, D&C Red n° 7 Zirconium lake, D&C Red n° 8 Sodium lake, D&C Red n° 9 Aluminum lake, D&C Red n° 9 Barium lake, D&C Red n° 9 Barium/Strontium lake, D&C Red n° 9 Zirconium lake, D&C Red n° 10 Sodium lake, D&C Red n° 19 Aluminum lake, D&C Red n° 19 Barium lake, D&C Red n° 19 Zirconium lake, D&C Red n° 21 Aluminum lake, D&C Red n° 21 Zirconium lake, D&C Red n° 22 Aluminum lake, D&C Red n° 27 Aluminum lake, D&C Red n° 27 Aluminum/Titanium/Zirconium lake, D&C Red n° 27 Barium lake, D&C Red n° 27 Calcium lake, D&C Red n° 27 Zirconium lake, D&C Red n° 28 Aluminum lake, D&C Red n° 28 Sodium lake D&C Red n° 30 lake, D&C Red n° 31 Calcium lake, D&C Red n° 33 Aluminum lake, D&C Red n° 34 Calcium lake, D&C Red n° 36 lake, D&C Red n° 40 Aluminum lake, D&C Blue n° 1 Aluminum lake, D&C Green n° 3 Aluminum lake, D&C Orange n° 4 Aluminum lake, D&C Orange n° 5 Aluminum lake, D&C Orange n° 5 Zirconium lake, D&C Orange n° 10 Aluminum lake, D&C Orange n° 17 Barium lake, D&C Yellow n° 5 Aluminum lake, D&C Yellow n° 5 Zirconium lake, D&C Yellow n° 6 Aluminum lake, D&C Yellow n° 7 Zirconium lake, D&C Yellow n° 10 Aluminum lake, FD&C Blue n° 1 Aluminum lake, FD&C Red n° 4 Aluminum lake, FD&C Red n° 40 Aluminum lake, FD&C Yellow n° 5 Aluminum lake, FD&C Yellow n° 6 Aluminum lake.

The chemistry material corresponding to each of these organic colorants previously cited are mentioned in the book called <<International Cosmetic Ingredient Dictionnary and Handbook>>, Edition 1997, pages 371 to 386 and 524 to 528, published by <<The Cosmetic, Toiletry, and Fragrance Association>>, of which the content is hereby incorporated by reference in the present specification.

According to a preferred embodiment, the lake(s) is/are selected from carmin of cochineal and the water-insoluble salts of sodium, potassium, calcium, barium, aluminum, zirconium, strontium, titanium, of acid colorants such as azoic, anthraquinonic, indigoid, xanthenic, pyrenic, quinolinic, triphenylmethane, fluoran colorants, being given that these colorants may include at least one carboxylic or sulfonic acid group, and their mixture.

According to a preferred embodiment, the lake(s) is/are selected from carmin of cochineal and the water-insoluble salts of sodium, calcium, aluminum, and their mixture.

As lake incorporating carmine we may cite the commercial references: CARMIN COVALAC W 3508, CLOISONNE RED 424C et CHROMA-LITE MAGENTA CL4505.

The water-insoluble aluminum salts are preferably selected from FDC Yellow N° 5 aluminum lake, le FDC Blue N° 1 aluminum lake, le FDC Red N° 40 aluminum lake, le FDC Red N° 30 aluminum lake, le FDC Green N° 5 aluminum lake, and their mixtures. As compound incorporating such inorganic lake may notably be cited the commercial references: INTENZA FIREFLY C91-1211, INTENZA AZURE ALLURE C91-1251, INTENZA THINK PINK C91-1236

The water-insoluble calcium salts are preferably selected from Red N° 7 calcium lake. As compound incorporating such inorganic lake may notably be cited the commercial references: INTENZA MAGENTITUDE C91-1234, INTENZA HAUTE PINK C91-1232, INTENZA RAZZLED ROSE C91-1231, INTENZA AMETHYST FORCE C91-7231, INTENZA PLUSH PLUM C91-7441, INTENZA ELECTRIC CORAL C91-1233, FLORASOMES-JOJOBA-SMS-10% CELLINI RED-NATURAL and their mixture.

The water-insoluble sodium salts are preferably selected from Red N° 6 sodium lake and Red N° 28 sodium lake, and their mixture. E As compound incorporating such inorganic lake may notably be cited the commercial references: INTENZA MANGO TANGO C91-1221 and INTENZA NITRO PINK C91-1235.

In preferred embodiments, the colorant is an inorganic colorant.

In a preferred embodiment, the colorant is a metallic oxide. Such metallic oxide is preferably selected from iron oxides, titanium oxides, and mixtures thereof.

The color-changing compositions of the invention may comprise a mixture of two or more colorants, either encapsulated individually in microcapsules and/or one or more blends of colorants encapsulated within the multi-layer microcapsules.

In accordance with this specific embodiment, each layer of the microcapsule may contain at least one specific colorant or a specific blend of colorant(s).

In accordance with this specific embodiment, the color-changing composition of the invention comprises two or more microcapsules of the invention having different colors.

A person skilled in the art knows how to choose colorants and combinations of colorants to produce a desired color effect or color change.

As stated previously, the microcapsules of the invention contain preferably at least titanium dioxide and/or iron oxides in their coating, preferably at least titanium dioxide.

In a preferred embodiment, the microcapsules of the invention contain preferably at least titanium dioxide and iron oxides in their coating.

According to a specific embodiment, the outer layer of said microcapsules contains titanium dioxide and more preferably as only colorant.

According to a specific embodiment, the composition according to the invention is non-colored, "non-colored" or "uncolored" composition meaning a transparent or white composition.

According to a preferred embodiment the composition according to the present invention, comprises uncoloured microcapsules, that is the outer layer being white or transparent, and when the outer layer is transparent, the visible inner layer is white. For the purposes of the invention, the term "transparent composition" means a composition which transmits at least 40% of light at a wavelength of 750 nm without scattering it, i.e. a composition in which the scattering angle of the light is less than 5° and is better still about 0°.

The transparent composition may transmit at least 50%, especially at least 60% and especially at least 70% of light at a wavelength of 750 nm.

The transmission measurement is made with a Cary 300 Scan UV-visible spectrophotometer from the company Varian, according to the following protocol:
- the composition is poured into a square-sided spectrophotometer cuvette with a side length of 10 mm;
- the sample of the composition is then maintained in a thermostatically-regulated chamber at 20° C. for 24 hours;
- the light transmitted through the sample of the composition is then measured on the spectrophotometer by scanning wavelengths ranging from 700 nm to 800 nm, the measurement being made in transmission mode;
- the percentage of light transmitted through the sample of the composition at a wavelength of 750 nm is then determined.

The transparent compositions, when they are placed 0.01 m in front of a black line 2 mm thick in diameter drawn on a sheet of white paper, allow this line to be seen; in contrast, an opaque composition, i.e. a non-transparent composition, does not allow the line to be seen.

According to a specific embodiment, the outer layer of said microcapsules contains organic pigments or iron oxides.

The colorants are present in amounts ranging from 20% to 90% by weight, preferably from 30% to 80% by weight, more preferably from 50% to 75% by weight relative to the total weight of the microcapsule.

In a particular embodiment, the microcapsules contain metallic oxides selected from iron oxides, titanium oxides, and mixtures thereof, present in an amount ranging from 20% to 90% by weight, preferably from 30% to 85% by weight, more preferably from 50% to 85% by weight relative to the total weight of the microcapsule.

In particular the titanium oxide may be present from 28% to 80% by weight, preferably from 30% to 75% by weight, and more preferably from 30 to 50% by weight, relative to the total weight of the microcapsule.

In a particular embodiment, the microcapsule according to the invention comprises titanium dioxide in an amount from 50% to 80%, in particular from 55% to 70%, and in particular from 55% to 65% by weight, relative to the total weight of the microcapsule.

In particular the iron oxides may be present from 5% to 75% by weight, preferably 8% to 65% by weight relative to the total weight of the microcapsule. In a particular embodiment, the iron oxides are present in an amount higher than 15% by weight, preferably higher than 30% by weight, and in particular from 40% to 65% by weight relative to the total weight of the microcapsule.

In a preferred embodiment, in at least one layer, and preferably in every layer, the colorants are the main ingredients, i.e. represent at least 40% by weight of the layer(s), preferably at least 75% by weight of the layer(s), more preferably at least 95% by weight of the layer(s).

In a preferred embodiment the mean thickness of the titanium dioxide layer ranges from 5 μm to 150 μm.

Lipid-Based Material

The inner and/or outer layer(s) may also include advantageously at least one lipid-based material.

According to a particular embodiment of this invention, such a lipid-based material may have amphiphilic properties, that is to say having an apolar part and a polar part.

Such lipid-based material can include at least one or several $C_{12}$-$C_{22}$ fatty acid chain(s) such as those selected from stearic acid, palmitic acid, oleic acid, linoleic acid, linolenic acid, etc., and mixtures thereof. Preferably these fatty acids chains are hydrogenated. Eventually, these fatty acid chains may be the apolar part of a lipid-based material.

Such lipid-based material is preferably selected from phospholipids. These phospholipids are preferably selected from phosphoacylglycerol, more preferably selected from lecithins, and are in particular hydrogenated lecithin.

The lipid based material may represent from 0.05 to 5% by weight of the microcapsule, in particular from 0.1 to 1% by weight of microcapsule.

By combining three or more compounds (ex: sugar alcohols, polymers, lipid-based material) in the microcapsule of different hardness and/or water solubility, it is possible to adjust the time required for colorant-encapsulated microcapsules to break down on the skin so that, by varying the method or intensity of application onto the skin, it is possible to adjust the preferred colouration or gradation pattern.

Thus, according to a preferred embodiment, the multi-layer coating contains at least starch as polymer and at least one lipid-based material, which is preferably lecithin.

According to an advantageous embodiment the microcapsules according to the invention include at least one monosaccharide or its derivative and at least one polysaccharide or its derivatives.

According to a preferred embodiment, the microcapsules include a core comprising a monosaccharide derivative and a coating comprising a polysaccharide (or its derivative) including one type of ose or several type of ose(s), preferably several types of oses.

According to a more preferably embodiment, the microcapsules include a core comprising a monosaccharide polyol, preferably selected from mannitol, erythritol, xylitol, sorbitol, and a coating comprising a polysaccharide (or its derivative) including as ose(s) at least one or more D-Glucose unit(s).

According to a preferred embodiment, the microcapsules include three or more colorants in different layers.

According to a preferred embodiment, the microcapsules additionally include a lipid-based material chosen from phospholipids, advantageously selected from phosphoacylglycerol and in particular from lecithins.

In a particular embodiment, the microcapsule contains mannitol, starch polymer and a lipid-based material.

Referring to FIG. 1, according to a preferred embodiment, the present invention advantageously provides a color-changing microcapsule having a size ranging from 10 μm to 800 μm, preferably from 50 μm to 600 μm and more preferably from 60 μm to 250 μm in diameter of the microcapsule, comprising:

i) a core (A), preferably having a size ranging from 500 nm to 150 μm in diameter, which preferably does not contain any colorant, and comprising at least one organic core preferably selected from at least one sugar alcohol preferably a monosaccharide-polyol advantageously selected from mannitol, erythritol, xylitol, sorbitol, and mixture thereof;

ii) one first layer (B) surrounding said core comprising:
at least one colorant, preferably iron oxide(s), and
a binder selected from at least one polymer, at least one lipid-based material, and their mixture, preferably their mixture;

iii) one second layer (C) surrounding said first layer (B), preferably having a thickness of 5 to 500 μm, comprising:
titanium dioxide particles, and
a binder selected from at least one polymer, at least one lipid-based material, and their mixture, preferably their mixture;

iv) optionally one third layer (D) surrounding said second layer (C) comprising:
at least one colorant, and
a binder selected from at least one polymer, at least one lipid-based material, and their mixture, preferably their mixture;

v) optionally one fourth layer (E) surrounding said third layer (D), if any, or surrounding said second layer (C) comprising
at least one wall-forming polymer preferably selected from polysaccharides such as cellulose derivatives, in particular cellulose ether and cellulose ester, from (poly)(alkyl)(meth)acrylic acid and derivatives, notably (poly)(alkyl)(meth)acrylate and derivatives, and preferably from alkylacrylic/alkylmethacrylic acid copolymers and their derivatives.

In a preferred embodiment, the polymer is a hydrophilic polymer selected from the group consisting of starch and its derivatives, in particular corn starch.

As examples of commercially available microcapsules to be used in the composition of the invention, we may refer to the following microcapsules produced by Korea Particle Technology KPT under the commercial names:
Magic50-BW0105 from KPT: ash gray spherical microcapsule containing mannitol, iron oxide red, iron oxide yellow, iron oxide black, hydrogenated lecithin, titanium dioxide, zea mays (corn) starch, having 60-200 Mesh particle size.

The microcapsules suitable for the present invention are stable into the compositions according to the present invention, preferably at high temperatures, for instance greater than or equal to 40° C., for example for one month, better two months and still better three months in an oven at 45° C. or for 15 days in an oven at 60° C.

In a preferred embodiment, the microcapsules according to the present invention present an appropriate softening kinetics.

That is preferably, at least three hours after being in contact with the other compounds of the formula, the hardness of the microcapsules is advantageously from 5 to 50 grams, more preferably from 6 to 20 grams and still more preferably from 7 to 10 grams. Such hardness is in conformity with an industrial process for preparing the cosmetic compositions including such microcapsules.

Such values of softening kinetics and hardness allow to provide not only aesthetic microcapsules but also overall aesthetic compositions.

Particularly, the composition may lead to different shades or color gradations depending on the intensity of the rubbing. The compositions may advantageously present a high chromaticity C* as measured in the in CIE Lab system 1976.

Stabilizing System

A stated previously, the stability of the microcapsules containing releasable colorant(s) is achieved according the invention by using at least one gelifying hydrophilic agent chosen from neutralized and crosslinked acrylic homopolymers or copolymers preferably in non-particulate form.

This hydrophilic agent is a non-emulsifying agent.

Advantageously the composition according to the invention may also comprise an additional hydrophilic gelifying agent chosen 2-acrylamido-2-methylpropanesulphonic acid polymers preferably a 2-acrylamido-2-methylpropanesulphonic acid homopolymer.

When the composition according to the invention comprises a neutralized and crosslinked acrylic homopolymers or copolymers and a 2-acrylamido-2-methylpropanesulphonic acid homopolymer, the stabilizing system is a non-emulsifying system.

For the purposes of the present patent specification, the term "hydrophilic agent" means an agent in particular a (co)polymer that is capable of forming hydrogen bond(s) with water or alcohol compounds, in particular chosen from lower alcohols, glycols, polyols. In particular, polymers are concerned which are capable of forming O—H, N—H and S—H bonds.

a) Neutralized and Crosslinked Acrylic Homopolymers or Copolymers in Non-Particulate Form The crosslinked acrylic polymers employed in the composition according to the invention are neutralized prior to being used in the composition; that is to say, they are sold in neutralized form, in contrast to the acrylic polymers in non-neutralized form, which are neutralized in situ when the composition is formulated, by addition of a base.

Examples of these crosslinked acrylic polymers which are already neutralized before being used, or otherwise, include:
Cosmedia SP® or crosslinked sodium polyacrylate containing 90% of dry substance and 10% of water,
partially neutralized, crosslinked sodium polyacrylates which are in the form of an inverse emulsion containing at least one polar oil, an example being that sold under the name Luvigel® EM by BASF; and
mixtures thereof.

In a preferred embodiment, the composition of the invention comprises at least a partially neutralized, crosslinked sodium polyacrylates which are in the form of an inverse emulsion containing at least one polar oil, and preferably the product sold under the name Luvigel® EM by BASF.

A crosslinked acrylic acid polymer in accordance with the present invention that has not been neutralized beforehand may be neutralized by any appropriate means, and in particular by addition of sodium hydroxide. This gives sodium polyacrylates. Potassium polyacrylates are also suitable for the present invention.

In reality the neutralization may be carried out prior to use in the composition of the invention, if the polymer in question is sold in a non-neutralized form. In contrast, for some of these compounds, the neutralization is inherent in the primary substance. This is the case in particular with Luvigel® EM and the product called Cosmedia® SP, which are already partially neutralized.

The neutralizing step, with sodium or potassium counterions for example, is necessary in order to give the crosslinked acid polymers their property of gelling and hence of stabilizing the composition. Said crosslinked acrylic polymers are converted into corresponding acrylate polymers during this neutralizing step. The acrylic monomers of the crosslinked acrylic polymer according to the invention may be neutralized to a degree of 5% to 80%.

In one particular embodiment of the invention, the crosslinked acrylic polymer according to the invention may comprise ionic monomers. Ionic monomers which may be employed include acrylamide, methacrylamide, vinylpyrrolidone, vinylimidazole, vinylcarpolactam and hydroxyalkyl esters of carboxylic acids, such as hydroxyethyl acrylates. A particular instance of ionic monomers are unsaturated $C_3$-$C_5$ carboxylic acids. However, in the context of the present invention, preference is given to crosslinked acrylic polymers containing more than 90% of acrylic acid monomers, or even containing no nonionic monomer.

In one particular embodiment the crosslinked acrylic acid homopolymer or copolymer may be in the form of a water-in-oil emulsion, termed an inverse emulsion. This inverse emulsion may be obtained, for example, by polymerization in inverse emulsion.

In one particular embodiment of the invention, the polymer employed is a partially neutralized, crosslinked sodium polyacrylate which is in the form of an inverse emulsion comprising at least one polar oil. Oils that may be mentioned include fatty acid esters. Examples of these fatty acid esters are isopropyl esters of fatty acids, such as isopropyl palmitate or isopropyl myristate, or polyglycerides of fatty acids, especially mixtures of fatty acids containing at least 50% of capric and/or caprylic acids. Water-in-oil emulsions of these kinds are described in document U.S. Pat. No. 6,197,283, which is incorporated by reference in the present application.

Thus the polymer is a partially neutralized, crosslinked sodium polyacrylate in an inverse emulsion comprising at least one fatty acid esters preferably at least one isopropyl esters of fatty acids, such as isopropyl palmitate or isopropyl myristate, or polyglycerides of fatty acids, especially mixtures of fatty acids containing at least 50% of capric and/or caprylic acids.

In this embodiment the oily phase may be composed of one or more fatty acid esters, one or more fatty acid polyglycerides based on a mixture of polyglycerides, which contains diglycerides and triglycerides, with mixtures of fatty acids, which contain caprylic acid and/or capric acid, preferably in a proportion of at least 50% by weight, relative to the total weight of fatty acids.

In one embodiment of the invention the oil content of the inverse emulsion is between 10% and 70% by weight, in particular between 15% and 35% by weight, relative to the total weight of the inverse emulsion.

On this point, mention is made in particular of Luvigel® EM, whose oily phase contains 26% of oil phase composed of $C_8$-$C_{10}$ triglycerides, namely triglycerides whose fatty acids are a mixture of capric and caprylic acids The at least partially neutralized, crosslinked acrylic polymer may be present in the inverse emulsion in an amount of from 20% to 70% by weight, in particular from 20% to 65% by weight, for example from 20% to 62% by weight, relative to the total weight of the inverse emulsion.

In particular, in one embodiment, the crosslinked acrylic polymer may be present in the inverse emulsion in an amount of from 20% to 30% by weight, relative to the total weight of the inverse emulsion. In yet another embodiment the crosslinked acrylic polymer may be present in the inverse emulsion in an amount of from 50% to 62% by weight, relative to the total weight of the composition.

The polymers in accordance with the invention may be composed of
  a) from 35% to 100% by weight of ionic monomers, the ionic monomers being 5-80% neutralized;
  b) from 0% to 65% by weight of nonionic monomers;
  c) from 0.3 to 1 mol %, relative to a) and b), of at least one at least difunctional monomer.

In the water-in-oil formulation of such a polymer, the oily phase may then be composed of one or more fatty acid esters as described above.

The acrylic acid may be crosslinked by any method known to a person skilled in the art, in particular as per the description of document U.S. Pat. No. 6,197,283 or as per the description of document U.S. Pat. No. 6,444,785, which refers to the crosslinking agents that can be used.

Among these, mention is made of the compounds containing an unsaturation that is soluble in water or in oil. Crosslinking agents of these kinds are, in particular, methylenebisacrylamide, divinylpyrrolidone, alkyl (meth)acrylate, triallylamine, ethylene glycol diacrylates (up to 50 EO), (meth)acrylic esters with dihydric or polyhydric alcohols, such as trimethylolpropane triacrylate or pentaerythritol tetraacrylate.

In one embodiment the crosslinking agent is soluble in water.

In another embodiment the crosslinking agent is triallylamine.

W/O emulsions containing a polymer in accordance with the present invention may be prepared in accordance with the teaching of document U.S. Pat. No. 6,444,785, incorporated here by reference. The objective of this process is to lower the residual monomer content by post-treatment with a redox initiator system. According to that process, the post-treatment of the W/O emulsion is carried out by adding a redox initiator system which comprises essentially:
  a) 0.001% to 5% by weight, relative to the total amount of monomers used for the preparation of the polymer,
    a1) of an oxidizing agent $R^1OOH$,
    in which $R^1$ denotes hydrogen, a $C_1$ to $C_8$ alkyl group or a $C_6$ to $C_{12}$ aryl group, and/or
    a2) of a compound which releases hydrogen peroxide in aqueous medium, and
  b) 0.005% to 5% by weight, relative to the total amount of monomers used for the preparation of the polymer,
    b1) of an α-hydroxycarbonyl compound

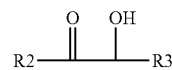

in which the groups have, independently of one another, the following meaning:

R2: hydrogen, a $C_1$-$C_{12}$ alkyl group which optionally contains functional groups and/or may contain olefinic unsaturations, R3: hydrogen, OH, a $C_1$-$C_{12}$ alkyl group which optionally contains functional groups and/or may contain olefinic unsaturations, and R2 and R3 may form a cyclic structure, which may contain a heteroatom and/or functional groups, and/or may contain olefinic unsaturations, and/or b2) of a compound which liberates an α-hydroxycarbonyl compound of this kind in aqueous medium, and c) catalytic amounts of a multivalent metal ion which is able to exist in a plurality of valence states.

The amount of at least partially neutralized, crosslinked acrylic homopolymer(s) or copolymer(s) ranges, for example, in terms of active material, from 0.1 to 2.5% by weight, preferably from 0.2 to 1% by weight, better still from 0.3 to 0.8%, relative to the total weight of the composition.

The amount of at least partially neutralized, crosslinked acrylic homopolymer(s) or copolymer(s) ranges, for example, from 0.5 to 3% by weight, preferably from 0.7 to 2.5% by weight, better still from 1 to 2%, by weight, relative to the total weight of the composition.

b) 2-acrylamido-2-methylpropanesulphonic acid polymers

The emulsion according to the invention may contain one or more 2-acrylamido-2-methylpropanesulphonic acid polymers.

In the present application, the expression "polymer comprising 2-acrylamido-2-methylpropanesulphonic acid units" (AMPS) is intended to mean both homopolymers and copolymers, and both crosslinked polymers and non-crosslinked polymers.

Preferably the at least one 2-acrylamido-2-methylpropanesulphonic acid polymer is a 2-acrylamido-2-methylpropanesulphonic acid homopolymer.

They are water-soluble or water-dispersible or water-swellable polymers.

Preferably, the AMPS polymers used in accordance with the invention may be partially or completely neutralized with an inorganic base (sodium hydroxide, potassium hydroxide, aqueous ammonia) or an organic base such as mono-, di- or triethanolamine, an aminomethylpropanediol, N-methylglucamine or basic amino acids such as arginine and lysine, and mixtures of these compounds. They are generally neutralized. In the present invention, the term "neutralized" is intended to mean polymers that have been completely or almost completely neutralized, i.e. at least 90% neutralized.

The AMPS polymers used in the composition of the invention generally have a number-average molecular weight ranging from 1000 to 20 000 000 g/mol, preferably ranging from 20 000 to 5 000 000, and even more preferably from 100 000 to 1 500 000 g/mol.

When the polymers are crosslinked, the crosslinking agents may be chosen from compounds with an olefinic polyunsaturation commonly used for crosslinking polymers obtained by radical polymerization. As crosslinking agents, mention may, for example, be made of divinylbenzene, diallyl ether, dipropylene glycol diallyl ether, polyglycol diallyl ethers, triethylene glycol divinyl ether, hydroquinone diallyl ether, ethylene glycol di(meth)acrylate, tetraethylene glycol di(meth)acrylate, trimethylolpropane triacrylate, methylenebisacrylamide, methylenebismethacrylamide, triallylamine, triallyl cyanurate, diallyl maleate, tetraallylethylenediamine, tetraallyloxyethane, trimethylolpropane diallyl ether, allyl (meth)acrylate, allyl ethers of alcohols of the sugar series, or other allyl or vinyl ethers of polyfunctional alcohols, and also allyl esters of phosphoric acid derivatives and/or vinylphosphonic acid derivatives, or mixtures of these compounds. According to a preferred embodiment of the invention, the crosslinking agent is chosen from methylenebisacrylamide, allyl methacrylate and trimethylolpropane triacrylate (TMPTA). The degree of crosslinking generally ranges from 0.01 to 10 mol %, and more particularly from 0.2 to 2 mol %, relative to the polymer.

The AMPS homopolymers preferred for use in the composition of the invention are crosslinked and neutralized, and they can be obtained according to the preparation process comprising the following steps:

(a) 2-acrylamido-2-methylpropanesulphonic acid in free form is dispersed or dissolved in a solution of tert-butanol or of water and tert-butanol;

(b) the solution or the dispersion of monomer obtained in (a) is neutralized with one or more inorganic or organic bases, preferably aqueous ammonia $NH_3$, in an amount that makes it possible to obtain a degree of neutralization of the sulphonic acid functional groups of the polymer ranging from 90% to 100%;

(c) the crosslinking monomer(s) is (are) added to the solution or dispersion obtained in (b);

(d) a conventional radical polymerization is carried out in the presence of free radical initiators at a temperature ranging from 10 to 150° C.; the polymer precipitating from the tert-butanol-based solution or dispersion.

The AMPS homopolymers that are more particularly preferred comprise, distributed randomly, units of general formula (I) below:

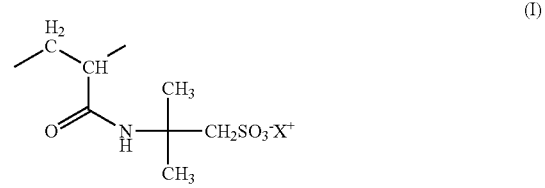

in which $X^+$ denotes a proton, an alkali metal cation, an alkaline earth metal cation or the ammonium ion, it being possible for no more than 10 mol % of the $X^+$ cations to be $H^+$ protons;

and crosslinking units originating from at least one monomer having at least two olefinic double bonds.

The homopolymers used according to the invention and that are more particularly preferred comprise from 90% to 99.9% by weight, and preferably from 98% to 99.5% by weight of units of formula (I), and from 0.01% to 10% by weight, preferably from 0.2% to 2% by weight of crosslinking units, the proportions by weight being defined relative to the total weight of the polymer.

As a preferred homopolymer of this type, mention may be made of the crosslinked and neutralized 2-acrylamido-2-methylpropanesulphonic acid homopolymer sold by the company Clariant under the trade name "Hostacerin AMPS" (INCI name: Ammonium Polyacryldimethyltauramide).

The 2-acrylamido-2-methylpropanesulphonic acid (AMPS) copolymers that can be used in the composition of the invention may be chosen in particular from:

1) crosslinked anionic copolymers of acrylamide or methacrylamide and of 2-acrylamido-2-methylpropanesulphonic acid, in particular those which are in the form of a W/O emulsion, such as those sold under the name Sepigel 305 by the company Seppic (INCI name: Polyacrylamide/C13-14 Isoparaffin/Laureth-7), or under the name Simulgel 600 by the company Seppic (INCI name: Acrylamide/Sodium acryloyldimethyltaurate copolymer/isohexadecane/Polysorbate 80), 2) copolymers of (meth)acrylic acid or of (meth)acrylate and of 2-acrylamido-2-methylpropanesulphonic acid, in particular those which are in the form of a W/O emulsion, such as those sold under the name Simulgel NS by the company Seppic (copolymer of sodium acrylamido-2-methylpropanesulphonate/hydroxyethyl acrylate in an inverse emulsion at 40% in polysorbate 60 and squalene) (INCI name: Hydroxyethyl acrylate/sodium acryloyldimethyltaurate copolymer/squalene/polysorbate 60) or those sold under the name Simulgel EG by the company Seppic (copolymer of acrylic acid/acrylamido-2-methylpropanesulphonic acid in the form of a sodium salt in an inverse emulsion at 45% in isohexadecane/water) (INCI name: sodium acrylate/sodium acryloyldimethyltaurate copolymer/i sohexadecane/Polysorbate 80), 3) copolymers of 2-acrylamido-2-methylpropanesulphonic acid and of vinylpyrrolidone or of vinylformamide, such as the products sold under the names Aristoflex AVC by the company Clariant, 4) copolymers of 2-acrylamido-2-methylpropanesulphonic acid containing a hydrophobic unit, in particular the copolymers comprising a 2-acrylamido-2-methylpropanesulphonic acid unit of formula (I) as defined above, and at least one hydrophobic unit of formula (II)

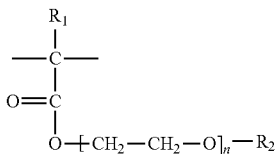

(II)

in which n denotes a number of moles which is an integer ranging from 3 to 100, preferably from 3 to 50, and more preferably from 7 to 25, $R_1$ is hydrogen or a methyl radical, and $R_2$ denotes a linear or branched alkyl radical containing from 6 to 30 carbon atoms, preferably from 10 to 22 carbon atoms, and better still from 14 to 22 carbon atoms.

In these copolymers, the AMPS unit of formula (I) represents in general from 80 to 99 mol %, and preferably from 85 to 99 mol %, and the unit of formula (II) represents in general from 1 to 20 mol %, and preferably from 1 to 15 mol %.

As AMPS copolymers containing a hydrophobic unit, mention may in particular be made of the copolymer of AMPS and of ethoxylated $C_{12}$-$C_{14}$ alkyl methacrylate (non-crosslinked copolymer obtained from Genapol LA-070 and from AMPS) (INCI name: Ammonium Acryloyldimethyltaurate/Laureth-7 Methacrylate Copolymer) sold under the name Aristoflex LNC by the company Clariant, the copolymer of AMPS and of ethoxylated stearyl methacrylate (25 EO) (copolymer crosslinked with trimethylolpropane triacrylate, obtained from Genapol T-250 and from AMPS) (INCI name: Ammonium Acryloyldimethyltaurate/Steareth 25 Methacrylate Crosspolymer) sold under the name Aristoflex HMS by the company Clariant, and the copolymer of AMPS and of ethoxylated $C_{16}$-$C_{18}$ alkyl methacrylate (INCI name: Ammonium Acryloyldimethyltaurate/Steareth-8 Methacrylate Copolymer), a non-crosslinked copolymer obtained from Genapol T-080 and from AMPS, sold under the name Aristoflex SNC by the company Clariant.

The amount of 2-acrylamido-2-methylpropanesulphonic acid polymer(s) in the composition of the invention may range, for example, in terms of active material, from 0.1% to 8% by weight, preferably from 0.2% to 6% by weight, better still from 0.2% to 5%, preferably from 0.5% to 3% by weight, relative to the total weight of the composition.

In a particular embodiment, the composition of the invention is a O/W emulsion and the amount of 2-acrylamido-2-methylpropanesulphonic acid polymer(s) preferably homopolymer(s) is, in terms of active material, from 0.2% to 5% by weight, preferably from 0.5% to 3% by weight, and more preferably from 0.5% to 2% relative to the total weight of the composition.

As shown, in the following examples; the presence of the neutralized and crosslinked acrylic polymer in non-particulate form, optionally along with a 2-acrylamido-2-methylpropanesulphonic acid polymer, is particularly advantageous since it significantly improves the stability of the microcapsules containing releasable colorant(s) in an emulsion and more particularly in an Oil/Water type emulsion. It is noticed a significant decrease of the ruptured microcapsules after a storage in an emulsion for two months and at different temperatures.

Thus, according to a preferred embodiment, the composition of the invention is an Oil/Water emulsion, and contains as stabilizing system, from 0.3 to 0.8%, in terms of active material, of at least neutralized and crosslinked acrylic polymer preferably in non-particulate form and optionally from 0.5% to 2%, in terms of active material, of at least one 2-acrylamido-2-methylpropanesulphonic acid homopolymer.

The composition according to the invention may comprise one or more additional polymer(s). In a particular embodiment, the additional polymer(s) is/are hydrophilic polymer(s).

Such hydrophilic polymer(s) is/are soluble or dispersible in water or in alcohol compounds, in particular chosen from lower alcohols, glycols, polyols.

The hydrophilic polymer(s) may be chosen from the following polymer(s):

acrylic or methacrylic acid homopolymers or copolymers or salts and esters thereof and in particular the products sold under the names Versicol F or Versicol K by the company Allied Colloid, Ultrahold 8 by the company Ciba-Geigy, and polyacrylic acids of Synthalen K type, and salts, especially sodium salts, of polyacrylic acids (corresponding to the INCI name sodium acrylate copolymer);

polyacrylic acid/alkyl acrylate copolymers, preferably modified or unmodified carboxyvinyl polymers; the copolymers most particularly preferred according to the present invention are acrylate/$C_{10}$-$C_{30}$-alkylacrylate copolymers cf carbomer dans Exemples) (INCI name: Acrylates/$C_{10-30}$ Alkyl acrylate Crosspolymer) such as the products sold by the company Lubrizol under the trade names Pemulen TR1, Pemulen TR2, Carbopol 1382 and Carbopol ETD 2020, and even more preferentially Pemulen TR-2;

alkylacrylic/alkylmethacrylic acid copolymers and their derivatives notably their salts and their esters, such as the copolymer of ethyl acrylate, methyl methacrylate and low content of methacrylic acid ester with quaternary ammonium groups provided under the tradename of EUDRAGIT RSPO from Evonik Degussa;
polysaccharides and derivatives, such as:
Starch polymers and derivatives, eventually modified; in a preferred embodiment, the starch polymer is a natural starch;
optionally modified polymers of natural origin, such as xanthan and derivatives;
and the mixtures thereof.

Aqueous Phase

Preferably, the microcapsules of the invention need to be in contact with an aqueous phase comprising water.

The aqueous phase is preferably present in an amount of at least 3% by weight, preferably at least 5% by weight, more preferably at least 8% by weight and advantageously at least 10% by weight relative to the weight of the composition.

Advantageously, water is present in an amount of at least 20% by weight, preferably at least 30% by weight, more preferably at least 40% by weight relative to the weight of the composition. Generally water is present in an amount ranging from 20% to 90% by weight, preferably 30% to 85% by weight and more preferably from 40 to 80% by weight, relative to the weight of the composition.

Advantageously, the aqueous phase may be present in a content ranging from 30% to 99% by weight, preferably from 40% to 95% more preferably from 50% to 90% by weight relative to the total weight of the said composition.°

This aqueous phase is particularly advantageous for imparting and/or improving deformability to the microcapsules of the invention.

Advantageously this aqueous phase acts as a swelling agent or as a softening agent towards the microcapsules without breaking them. The microcapsules are not inert when placed in this aqueous phase either they swell: their diameter significantly increases with an optional softening of the microcapsules, or the microcapsules significantly soften without increasing of the diameter, they become more malleable and easier to break when applied onto the skin.

The aqueous phase used in the composition according to the invention is able to act on the softening kinetics of the microcapsules and more particularly it allows to obtain a good balance between softening kinetics and hardness.

As a consequence, said aqueous phase is particularly advantageous for softening the microcapsules suitable for the present invention, in an appropriate way, since said aqueous phase plays a role on softening kinetics of said microcapsules.

Advantageously this aqueous phase acts as a swelling agent or as a softening agent towards the microcapsules preferably without breaking them or without triggering colorant leakage.

The aqueous phase comprises advantageously a water-soluble solvent.

In the present invention, the term "water-soluble solvent" denotes a compound that is liquid at room temperature and water-miscible (miscibility with water of greater than 50% by weight at 25° C. and atmospheric pressure).

The water-soluble solvents that may be used in the composition of the invention may also be volatile.

As said, the composition of the invention contains an aqueous phase comprising water and at least one compound chosen among polyols, in particular glycols, $C_2$-$C_8$ monoalcohols and mixtures thereof. It also may contain $C_4$ ketones and $C_2$-$C_4$ aldehydes.

The composition of the invention contains microcapsules as defined above and an aqueous phase comprising water and at least one compound chosen from polyols, glycols, C2-C8 monoalcohols and mixtures thereof. Preferably the aqueous phase comprises water and the at least one compound chosen from polyols, glycols and the mixtures thereof.

The composition of the invention will generally comprise at least one compound chosen from polyols, glycols, $C_2$-$C_8$ monoalcohols, and mixtures thereof in amount ranging from 3% to 50% by weight, preferably from 5% to 45% by weight and more preferably from 10% to 45% by weight relative to the total weight of the composition.

In a preferred embodiment, the aqueous phase suitable for the present invention comprises at least one C2-C8 monoalcohols.

In another preferred embodiment, the aqueous phase suitable for the present invention comprises at least one polyol particularly a glycol.

Monoalcohols or Lower Alcohols

Monoalcohol or lower alcohol that is suitable for use in the invention may be a compound of linear, branched or cyclic, saturated or unsaturated alkyl type, bearing only one —OH function.

Advantageously, C2-C8 monoalcohols are non cyclic monoalcohols, still preferably they are C2-C5 monoalcohols and preferably C2-C3 monoalcohols.

The lower monoalcohols that are advantageously suitable for formulating a composition according to the present invention are those especially containing from 2 to 5 carbon atoms such as ethanol, propanol, butanol, isopropanol, isobutanol preferably ethanol and/or isopropanol and more preferably at least ethanol.

A composition of the invention may comprise at least 1% by weight, preferably at least 2%, more preferably from 2% to 15%, advantageously from 3% to 10%, by weight and better still from 3% to 8% by weight, preferably from 4% to 6% by weight of mono-alcohol(s) relative to the total weight of said composition.

There is also a need to have emulsions containing changing color microcapsules in a physiological medium comprising a lower alcohol because some cosmetic ingredients are particularly soluble in hydroalcoholic media.

Furthermore, the lower monoalcohols such as ethanol allow to dissolve active agents, especially keratolytic agents, such as, for example, salicylic acid and its derivatives.

Some microcapsules of the prior art rapidly disintegrate in hydroalcoholic media, as a consequence there was a need to have emulsions comprising changing color microcapsules stable in hydroalcoholic media.

Polyols

For the purposes of the present invention, the term "polyol" should be understood as meaning any organic molecule comprising at least two free hydroxyl groups. The term "polyol" according to the invention does not encompass monosaccharide-alcohol disclosed above.

Preferably, a polyol in accordance with the present invention is present in liquid form at room temperature.

The polyols/glycols are moisturizers or humectants.

They may have an effect towards the stability of other ingredients of the composition particularly towards microcapsules of the prior art.

There is thus a need to have at disposal stable compositions containing changing color microcapsules in a physiological medium comprising a polyol particularly a glycol because these compositions present a noticeable moisturizing or humecting effect.

This technical problem is solved by the compositions according to the invention. A polyol that is suitable for use in the invention may be a compound of linear, branched or cyclic, saturated or unsaturated alkyl type, bearing on each alkyl chain at least two —OH functions, in particular at least three —OH functions and more particularly at least four —OH functions.

The polyols that are advantageously suitable for formulating a composition according to the present invention are those especially containing from 2 to 32 carbon atoms preferably 2 to 20 carbon atoms and more preferably 2 to 16 carbon atoms, advantageously 2 to 10 carbon atoms, more advantageously 2 to 6 carbon atoms.

According to another embodiment, a polyol that is suitable for use in the invention may be advantageously chosen from polyethylene glycols.

According to one embodiment, a composition of the invention may comprise a mixture of polyols.

Advantageously, the polyol may be chosen from polyhydric alcohols, preferably of $C_2$-$C_8$ and more preferably $C_3$-$C_6$. The polyol may be chosen from glycerol, pentaerythritol, trimethylolpropane, ethylene glycol, propylene glycol, 1,3-butylene glycol, 1,3-propanediol, pentylene glycol, hexylene glycol, isoprene glycol, dipropylene glycol, diethylene glycol and diglycerol, and mixtures thereof, glycerol and derivatives thereof, polyglycerols, such as glycerol oligomers, for instance diglycerol, and polyethylene glycols, glycol ethers (especially containing from 3 to 16 carbon atoms) such as mono-, di- or tripropylene glycol ($C_1$-$C_4$)alkyl ethers, mono-, di- or triethylene glycol ($C_1$-$C_4$)alkyl ethers, and mixtures thereof.

Particularly, the polyol is selected from the group consisting in glycerol and glycols, preferably propylene glycol, butylene glycol, pentylene glycol, hexylene glycol, dipropylene glycol, diethylene glycol, ethylhexylglycerine, caprylyl glycol, glycol ethers, preferably mono-, di- or tripropylene glycol of alkyl($C_1$-$C_4$)ether or mono-, di- or triethylene glycol of alkyl($C_1$-$C_4$)ether, and mixtures thereof, more preferably glycerol. According to one preferred embodiment of the invention, the said polyol is chosen from ethylene glycol, pentaerythritol, trimethylolpropane, propylene glycol, butylene glycol, glycerol, polyglycerols and polyethylene glycols, and mixtures thereof.

In a particular embodiment, the polyol is selected from the group consisting in glycerol, and glycols chosen from propylene glycol, butylene glycol, ethylhexylglycerine, caprylyl glycol and mixtures thereof.

According to one particular embodiment, the composition of the invention comprises at least butylene glycol, glycerol or a mixture thereof.

In a preferred embodiment, the composition comprises at least glycerol.

According to one particular embodiment, the composition of the invention comprises glycerol as sole polyol.

Advantageously the composition may comprise from 1 to 10, preferably from 2 to 8 weight percent of glycerol based on the total weight of the composition.

Advantageously, the composition comprises from 5% to 50% by weight and in particular from 5% to 40%, and better from 6% to 30% by weight of polyol(s) and/or glycols based on weight of the aqueous phase.

Cosmetic Medium and Additional Ingredients

The composition according to the invention is cosmetically acceptable that is it contains a physiologically acceptable medium which is non toxic and appropriate to be applied on the keratin material of human beings.

"Cosmetically acceptable", in the sense of the present invention, means a composition with pleasant appearance, odor or feeling.

The "physiologically acceptable medium" is generally adapted to the form of under which the composition is intended to be conditioned.

Particularly the nature and the amount of the ingredients are adapted for example depending on whether the composition is formulated as a creamy emulsion or a fluid emulsion.

Depending upon the form and the aim of the skin care or make-up preparation, the composition of the invention will comprise, in addition to the microcapsules containing colorant, further additional cosmetic ingredient(s) such as the ones selected from volatile and non-volatile silicon or hydrocarbon oils, surfactants, fillers, additional gelifying agents, thickening agents, film forming agents, polymers, preservatives, silicone elastomere, additional non-entrapped colorants (ex: pigments, nacres . . . ), actives, UV sunscreens, perfumes, humectants, pH regulators and mixtures thereof.

In a particular embodiment, the composition contains silicone elastomer.

Suitable silicone elastomers include, for example, emulsifying silicone elastomers such as polyglycerolated and/or hydrophilic emulsifying silicone elastomers such as alkoxylated silicone elastomers, and non-emulsifying silicone elastomers. Such silicone elastomers can be spherical or non-spherical. In a particular embodiment, the composition may comprise a non emulsifying elastomer, in particular in the form of a powder. The amount of silicone elastomer may range from 0.1 to 10% by weight of active material, in particular from 0.2 to 3%, and more preferably from 0.2 to 1% by weight of the composition.

In another particular embodiment, the composition contains UV sunscreens. There are two groups of sunscreens: UVA sunscreens, which block UV radiation in the wavelength range of about 320 to 400 nm, and UVB sunscreens, which block radiation in the range of 290 to 320 nm. The compositions in accordance with the invention may comprise organic and/or inorganic UV sunscreen ingredients active in the UV-A and/or UV-B region which are hydrophilic and/or lipophilic.

The hydrophilic and/or lipophilic organic UV sunscreen ingredients are selected in particular from benzylidene camphor derivatives, dibenzoylmethane derivatives; cinnamic derivatives; salicylic derivatives; benzophenone derivatives; β,β-diphenylacrylate derivatives; p-aminobenzoic acid (PABA) derivatives; and their mixtures.

In another particular embodiment, the composition contains nacres.

The term "nacres" should be understood as meaning iridescent or non-iridescent coloured particles of any form, especially produced by certain molluscs in their shell or alternatively synthesized, which have a colour effect via optical interference.

The nacres may be selected from nacreous pigments such as mica coated with an iron oxide, mica coated with bismuth oxychloride, mica coated with Titanium oxide or dioxide, mica coated with chromium oxide, mica coated with tin oxide, mica coated with $SnO_2$, mica coated by $BaSO_4$, mica coated with an organic dye and also nacreous pigments based on bismuth oxychloride. Preferably, the nacres are white in their appearance, and they are formed preferably from mica coated with at least titanium dioxide.

As preferred nacres, we use mica coated with titanium oxide or dioxide.

In a particular embodiment, the composition contains at least one humectants. Humectants may be chosen from polyhydric alcohols, preferably of C2-C8 and more preferably C3-C6, preferably such as glycerol, propylene glycol, 1,3-butylene glycol, pentylene glycol, hexylene glycol, dipropylene glycol, diethylene glycol and diglycerol, and mixtures thereof.

In a preferred embodiment, the composition contains at least glycerol.

The pH of the cosmetic composition according to the present invention ranges preferably from 6 to 7.5. A preferred base to modify the pH is triethanolamine.

It is a matter of routine operations for a person skilled in the art to adjust the nature and amount of the additives present in the compositions in accordance with the invention such that the desired cosmetic properties thereof are not thereby affected.

This make up composition, which is preferably a makeup BB product for face or a foundation, provides very strong moisturizing sensation, creamy texture with very comfortable feeling during application, and sheer natural makeup result after application. After application, all these features help to deliver a very good balance of skincare efficacy perception (creamy and moisturization) as well as makeup efficacy (proper coverage and natural radiance). Advantageously, an appropriate sunscreen agent may be added.

Otherwise, the Emulsion may contain at least two different types of microcapsules for example three different types of microcapsules. Emulsion according to the invention can be obtained with pure and clean appearance of bulk, with perfect stability under −20/20° C. (5 cycle), room temperature (25° C., 2 months), 37° C. (2 months) and 45° C. (2 months). However, capsules would release pigments during application without any particle feeling. Makeup results are perfectly and evenly provided after application. Moreover, organic sun filter can be added in the system and provide additional sun care benefit.

Liquid Fatty Phase

Thus, a composition according to the invention may comprise at least one fatty phase that is liquid at room temperature and atmospheric pressure, and especially at least one oil as mentioned below.

Specifically, the presence of at least one oil is advantageous insofar as it facilitates the application of the composition and affords emollience.

According to the present invention, the term "oil" means a water-immiscible non-aqueous compound that is liquid at room temperature (25° C.) and at atmospheric pressure (760 mmHg).

An oily phase that is suitable for preparing an anhydrous cosmetic composition according to the invention may comprise hydrocarbon-based oils, silicone oils, fluoro oils or non-fluoro oils, or mixtures thereof.

The oils may be volatile or non-volatile.

They may be of animal, plant, mineral or synthetic origin. According to one embodiment variant, oils of plant origin are preferred.

The term "volatile oil" means any non-aqueous medium that is capable of evaporating on contact with the skin or the lips in less than one hour, at room temperature and atmospheric pressure. The volatile oil is a cosmetic volatile oil, which is liquid at room temperature. More specifically, a volatile oil has an evaporation rate of between 0.01 and 200 mg/cm$^2$/min, limits inclusive.

The term "non-volatile oil" means an oil that remains on the skin or the keratin fibre at room temperature and atmospheric pressure. More specifically, a non-volatile oil has an evaporation rate strictly less than 0.01 mg/cm$^2$/min.

To measure this evaporation rate, 15 g of oil or oil mixture to be tested are placed in a crystallizing dish 7 cm in diameter, placed on a balance that is in a large chamber of about 0.3 m$^3$ which is temperature-regulated, at a temperature of 25° C., and hygrometry-regulated, at a relative humidity of 50%. The liquid is allowed to evaporate freely, without stirring it, while providing ventilation by means of a fan (Papst-Motoren, reference 8550 N, rotating at 2700 rpm) placed in a vertical position above the crystallizing dish containing said oil or said mixture, the blades being directed towards the crystallizing dish, 20 cm away from the bottom of the crystallizing dish. The mass of oil remaining in the crystallizing dish is measured at regular intervals. The evaporation rates are expressed in mg of oil evaporated per unit of area (cm$^2$) and per unit of time (minutes).

For the purposes of the present invention, the term "silicone oil" means an oil comprising at least one silicon atom, and especially at least one Si—O group.

The term "fluoro oil" means an oil comprising at least one fluorine atom.

The term "hydrocarbon-based oil" means an oil mainly containing hydrogen and carbon atoms.

The oils may optionally comprise oxygen, nitrogen, sulfur and/or phosphorus atoms, for example in the form of hydroxyl or acid radicals.

a) Volatile Oils

The volatile oils may be chosen from hydrocarbon-based oils containing from 8 to 16 carbon atoms, and especially $C_8$-$C_{16}$ branched alkanes (also known as isoparaffins), for instance isododecane (also known as 2,2,4,4,6-pentamethylheptane), isodecane and isohexadecane, for instance the oils sold under the trade names Isopar® or Permethyl®, or especially linear $C_8$-$C_{14}$ alkanes.

Volatile oils that may also be used include volatile silicones, for instance volatile linear or cyclic silicone oils, especially those with a viscosity ≤8 centistokes (cSt) (8×10$^{-6}$ m$^2$/s), and especially containing from 2 to 10 silicon atoms and in particular from 2 to 7 silicon atoms, these silicones optionally comprising alkyl or alkoxy groups containing from 1 to 10 carbon atoms. As volatile silicone oils that may be used in the invention, mention may be made especially of dimethicones with viscosities of 5 and 6 cSt, octamethylcyclotetrasiloxane, decamethylcyclopentasiloxane, dodecamethylcyclohexasiloxane, heptamethylhexyltrisiloxane, heptamethyloctyltrisiloxane, hexamethyldisiloxane, octamethyltrisiloxane, decamethyltetrasiloxane and dodecamethylpentasiloxane, and mixtures thereof.

Volatile fluoro oils such as nonafluoromethoxybutane or perfluoromethylcyclopentane, and mixtures thereof, may also be used.

Advantageously, a liquid fatty phase of the invention may comprise from 1% to 50% by weight, preferably from 2% to 40% by weight and better still from 5% to 30% by weight of volatile oil(s) relative to the total weight of the said liquid fatty phase.

b) Non-Volatile Oils

The non-volatile oils may be chosen especially from nonvolatile hydrocarbon-based, fluoro and/or silicone oils.

Non-volatile hydrocarbon-based oils that may especially be mentioned include:
  hydrocarbon-based oils of animal origin,
  hydrocarbon-based oils of plant origin, such as phytostearyl esters, such as phytostearyl oleate, phytostearyl isostearate and lauroyl/octyldodecyl/phytostearyl glutamate (Ajinomoto, Eldew PS203), triglycerides formed from fatty acid esters of glycerol, in particular in which the fatty acids may have chain lengths ranging from $C_4$ to $C_{36}$ and especially from $C_{18}$ to $C_{36}$, these oils possibly being linear or branched, and saturated or unsaturated; these oils may especially be heptanoic or octanoic triglycerides, shea oil, alfalfa oil, poppy oil, millet oil, barley oil, rye oil, candlenut oil, passionflower oil, shea butter, aloe vera oil, sweet almond oil, peach stone oil, groundnut oil, argan oil, avocado oil, baobab oil, borage oil, broccoli oil, calendula oil, camellina oil, canola oil, carrot oil, safflower oil, flax oil, rapeseed oil, cotton oil, coconut oil, marrow seed oil, wheatgerm oil, jojoba oil, lily oil, macadamia oil, corn oil, meadowfoam oil, St John's Wort oil, monoi oil, hazelnut oil, apricot kernel oil, walnut oil, olive oil, evening primrose oil, palm oil, blackcurrant pip oil, kiwi seed oil, grapeseed oil, pistachio oil, winter squash oil, pumpkin oil, quinoa oil, musk rose oil, sesame oil, soybean oil, sunflower oil, castor oil and watermelon oil, and mixtures thereof, or alternatively caprylic/capric acid triglycerides, such as those sold by the company Stearineries Dubois or those sold under the names Miglyol 810®, 812® and 818® by the company Dynamit Nobel;

linear or branched hydrocarbons, of mineral or synthetic origin, such as liquid paraffins and derivatives thereof, petroleum jelly, polydecenes, polybutenes, hydrogenated polyisobutene such as Parleam, and squalanesynthetic ethers containing from 10 to 40 carbon atoms, such as dicaprylyl ether;

synthetic esters, for instance oils of formula $R_1COOR_2$, in which $R_1$ represents a linear or branched fatty acid residue containing from 1 to 40 carbon atoms, and $R_2$ represents a hydrocarbon-based chain that is especially branched, containing from 1 to 40 carbon atoms provided that $R_1+R_2 \leq 10$. The esters may be chosen especially from esters of alcohol and of fatty acid, for instance cetostearyl octanoate, esters of isopropyl alcohol, such as isopropyl myristate, isopropyl palmitate, isopropyl isostearate, ethyl palmitate, 2-ethylhexyl palmitate, isopropyl stearate, octyl stearate, hydroxylated esters, for instance isostearyl lactate, octyl hydroxystearate, alcohol or polyalcohol ricinoleates, hexyl laurate, neopentanoic acid esters, for instance isodecyl neopentanoate, isotridecyl neopentanoate, and isononanoic acid esters, for instance isononyl isononanoate and isotridecyl isononanoate, polyol esters and pentaerythritol esters, for instance dipentaerythrityl tetrahydroxystearate/tetrai sostearate, esters of diol dimers and of diacid dimers, such as Lusplan DD-DA5® and Lusplan DD-DA7® sold by the company Nippon Fine Chemical and described in patent application US 2004-175 338, copolymers of a diol dimer and of a diacid dimer and esters thereof, such as dilinoleyl diol dimer/dilinoleic dimer copolymers and esters thereof, for instance Plandool-G, copolymers of polyols and of diacid dimers, and esters thereof, such as Hailuscent ISDA or the dilinoleic acid/butanediol copolymer, fatty alcohols that are liquid at room temperature, with a branched and/or unsaturated carbon-based chain containing from 12 to 26 carbon atoms, for instance 2-octyldodecanol, isostearyl alcohol and oleyl alcohol, $C_{12}$-$C_{22}$ higher fatty acids, such as oleic acid, linoleic acid or linolenic acid, and mixtures thereof, dialkyl carbonates, the two alkyl chains possibly being identical or different, such as dicaprylyl carbonate sold under the name Cetiol CC® by Cognis, oils of high molar mass, in particular with a molar mass ranging from about 400 to about 2000 g/mol and in particular from about 650 to about 1600 g/mol. As oils of high molar mass that may be used in the present invention, mention may be made especially of linear fatty acid esters with a total carbon number ranging from 35 to 70, for instance pentaerythrityl tetrapelargonate, hydroxylated esters, such as polyglyceryl-2 triisostearate, aromatic esters, such as tridecyl trimellitate, esters of branched $C_{24}$-$C_{28}$ fatty alcohols or fatty acids, such as those described in U.S. Pat. No. 6,491,927, and pentaerythritol esters, and especially triisoarachidyl citrate, glyceryl triisostearate, glyceryl tris (2-decyl)tetradecanoate, polyglyceryl-2 tetraisostearate or pentaerythrityl tetrakis(2-decyl)tetradecanoate; phenyl silicones, such as Belsil PDM 1000 from the company Wacker (MM=9000 g/mol), non-volatile polydimethylsiloxanes (PDMS), PDMSs comprising alkyl or alkoxy groups that are pendent and/or at the end of the silicone chain, these groups each containing from 2 to 24 carbon atoms, phenyl silicones, for instance phenyl trimethicones, phenyl dimethicones, phenyl trimethylsiloxy diphenylsiloxanes, diphenyl dimethicones, diphenyl methyldiphenyl trisiloxanes and 2-phenylethyl trimethylsiloxysilicates, dimethicones or phenyl trimethicones with a viscosity of less than or equal to 100 cSt, and mixtures thereof; and also mixtures of these various oils, and mixtures thereof.

According to one embodiment, the composition of the invention comprises at least one non-volatile oil chosen from non-volatile hydrocarbon-based oils such as:

hydrocarbon-based oils of animal origin;

hydrocarbon-based oils of plant origin;

synthetic ethers containing from 10 to 40 carbon atoms;

synthetic esters, for instance oils of formula $R_1COOR_2$, in which $R_1$ represents a linear or branched fatty acid residue containing from 1 to 40 carbon atoms, and $R_2$ represents a hydrocarbon-based chain that is especially branched, containing from 1 to 40 carbon atoms provided that $R_1+R_2 \geq 10$;

polyol esters and pentaerythritol esters;

fatty alcohols that are liquid at room temperature, with a branched and/or unsaturated carbon-based chain containing from 12 to 26 carbon atoms;

dialkyl carbonates, the two alkyl chains possibly being identical or different;

oils of high molar mass; and mixtures thereof.

Advantageously, a liquid fatty phase of the invention may comprise at least 40% by weight, preferably at least 60% by weight or even 100% by weight of non-volatile oil(s) relative to the total weight of the said liquid fatty phase.

Galenic Formulation

A composition according to the invention may be in the form of makeup compositions and/or care compositions for keratin materials, in particular for skin or lips. Particularly a composition according to the invention may be a BB product or a foundation especially to be applied on the face or neck, a product for masking dark circles, a concealer product, a tinted cream, a colored composition for care or for making up the skin, especially for the face or body or an after-sun composition.

In a preferred embodiment, a composition according to the present invention is a non-rinsing composition: the composition is not intended to be rinsed after application on the skin.

In another preferred embodiment, the composition according to the present invention is not contained in a dispenser comprising a pump. This is advantageous since it avoids the risk for the microcapsules to be broken. Indeed, when using such a dispenser, said microcapsules could be crushed before their application on the keratin materials It is understood that the emulsions according to the invention can be in any galenical form conventionally used for topical application, especially in the form of liquid or semi-liquid consistency of the milk type, or of soft, semi-solid consistency of the cream or gel type, or alternatively a foam.

These compositions are prepared according to the usual methods.

The compositions of this type may be in the form of a facial and/or body care or makeup product, and may be conditioned, for example, in the form of cream in a jar or of fluid in a tube.

EXAMPLES

Microcapsules

Example 1: Preparation of a Microcapsule a Having Inner Brown Color Coating and Outer White Color Coating Mannitol (spray dried mannitol: Pearitol 100SD) is used as core.

To a mixed solution of 3200.0 g of ethanol, 120.0 g of ceramide (Ceramide PC 104) and 120.0 g of hydrogenated lecithin (Lipoid S 100-3) are added and completely dissolved at 40° C. To the resulting mixture, 1260.0 g of iron oxide yellow, 252.0 g of iron oxide red and 45.36 g of iron oxide black are added and well dispersed with a homogenizer to prepare an inner color coating solution.

347.70 g of Mannitol is introduced into a fluidized bed coating system (Glatt GPCG 1, bottom spray) as a seed and subjected to a coating at 500 ml/h of feeding rate of the inner color coating solution to obtain particles having a mannitol core coated with an inner color layer.

Thereafter, to a mixed solution of 1440.0 g of ethanol, 36.0 g of ceramide and 36.0 g of hydrogenated lecithin are added and dissolved at 40° C. To the resulting mixture, 600.0 g of titanium dioxide particles are added and well dispersed with a homogenizer to prepare a titanium dioxide particle coating solution.

A coating with the resulting titanium dioxide particle coating solution is realized by a fluidized bed process to obtain particles having an inner color layer coated with a titanium dioxide particle layer.

Then, 300.0 g of shellac is dissolved in 3000 g of ethanol to prepare an outer layer coating solution, which is coated onto the above titanium dioxide particle layer to obtain a color-changing microcapsule having a titanium dioxide particle layer coated with an outer layer.

Figure 1:
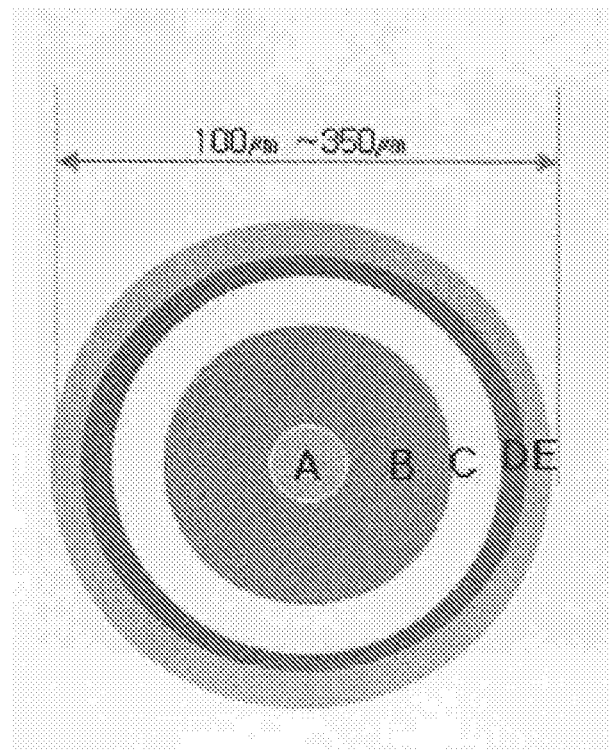
FIG. 1 is a schematic diagram illustrating a typical structure of a color-changing microcapsule of the present invention, wherein A represents a core and B, C, D and E being different layers concentrically surrounding said core.
Figure 2:
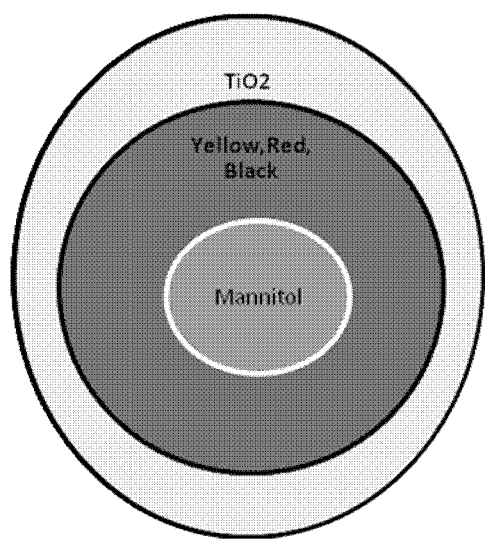
FIG. 2 represents a schematic diagram showing the core-shell structure of color-changing microcapsules B prepared according to Example 2 described below.

Example 2: Preparation of a Microcapsule B Having Inner Brown Color Coating and Outer White Color Coating By using the ingredients and contents described in the below table, a color-changing microcapsule having a core and 2 layers as shown in FIG. 1 is prepared by a fluidized bed process (according to a process similar to the one of example 1):

(1) Ingredients: Core seed—inner color layer —TiO$_2$ particle layer

| Core | Mannitol | 13.7% |
|---|---|---|
| 1$^{st}$ layer | Sunpuro Yellow | 17.36% |
| | Sunpuro Red | 3.67% |
| | Sunpuro Black | 0.61% |
| | Lecithin | 0.20% |
| | Corn Starch Binder | 1.0% |
| 2$^{nd}$ layer | Titanium dioxide | qsp. 100% |
| | Lecithin | 0.3% |
| | Corn Starch Binder | 1.5% |

Percentages indicate weight percent relative to the total microcapsule weight.

Compositions O/W Emulsions

| | | Example 1 according to invention % wgt | Example 2 according to invention % wgt | Example C (comparative) % wgt |
|---|---|---|---|---|
| A1 | CETYL ALCOHOL | 0.50 | 0.50 | 0.50 |
| | BEHENYL ALCOHOL | 1.00 | 1.00 | 1.00 |
| | PEG-100 STEARATE | 0.30 | 0.30 | 0.30 |
| | CETEARYL ALCOHOL (and) CETEARYL GLUCOSIDE | 0.32 | 0.32 | 0.32 |
| | ISOPROPYL ISOSTEARATE | 1.5 | 1.5 | 1.5 |
| | ETHYLHEXYL SALICYLATE | 8 | 8 | 8 |
| A2 | Ammonium Polyacryldimethyltauramide* | 1.00 | 0 | 0 |
| | CARBOMER | 0.07 | 0.07 | 0.07 |
| B | WATER | qs | qs | Qs |
| | DISODIUM EDTA | 0.10 | 0.10 | 0.10 |
| | DISODIUM STEAROYL GLUTAMATE | 0.50 | 0.50 | 0.50 |
| | GLYCERIN | 5.00 | 5.00 | 5.00 |
| C | WATER | 30.00 | 30.00 | 30.00 |
| D | Neutralized, crosslinked sodium polyacrylate in inverse emulsion at 26% with C8/C10 triglycerides (Luvigel from BASF)** | 1.00 | 2.00 | 0 |
| E | WATER | 5.00 | 5.00 | 5.00 |
| | TRIETHANOLAMINE | 0.75 | 0.75 | 0.75 |
| F | DIMETHICONE/VINYL DIMETHICONE CROSSPOLYMER (DC9701 powder by Dow Corning) | 0.80 | 0.80 | 0.80 |
| G | ALCOHOL DENAT. | 2.00 | 2.00 | 2.00 |
| | TOTAL | 100% | 100% | 100% |
| H | Microcapsule B | 3.00 | 3.00 | 3.00 |

|   |   | Example 3 according to invention % wgt | Example 4 according to invention % wgt |
|---|---|---|---|
| A1 | CETYL ALCOHOL | 0.50 | 0.50 |
|    | BEHENYL ALCOHOL | 1.00 | 1.00 |
|    | PEG-100 STEARATE | 0.30 | 0.30 |
|    | CETEARYL ALCOHOL (and) CETEARYL GLUCOSIDE | 0.32 | 0.32 |
|    | ISOPROPYL ISOSTEARATE | 1.5 | 1.5 |
|    | ETHYLHEXYL SALICYLATE | 8 | 8 |
| A2 | Ammonium Polyacryldimethyltauramide* | 1.00 | 0 |
|    | CARBOMER | 0.07 | 0.07 |
| B  | WATER | qs | qs |
|    | DISODIUM EDTA | 0.10 | 0.10 |
|    | DISODIUM STEAROYL GLUTAMATE | 0.50 | 0.50 |
|    | GLYCERIN | 5.00 | 5.00 |
| C  | WATER | 30.00 | 30.00 |
| D  | Neutralized, crosslinked sodium polyacrylate in inverse emulsion at 26% with C8/C10 triglycerides (Luvigel from BASF)** | 1.00 | 2.00 |
| E  | WATER | 5.00 | 5.00 |
|    | TRIETHANOLAMINE | 0.75 | 0.75 |
| F  | DIMETHICONE/VINYL DIMETHICONE CROSSPOLYMER (DC9701 powder by Dow Corning) | 0.80 | 0.80 |
| G  | ALCOHOL DENAT. | 2.00 | 2.00 |
|    | TOTAL | 100% | 100% |
| H  | Magic 50-BW0105 from KPT | 3.00 | 3.00 |

*crosslinked and neutralized 2-acrylamido-2-methylpropanesulphonic acid homopolymer sold by the company Clariant under the trade name "Hostacerin AMPS".
**= Luvigel EM from BASF at 25-26% by weight of neutralized, crosslinked sodium polyacrylate active substance in inverse emulsion with C8/C10 triglycerides 1. Protocol of Preparation:
1. Prepare phase B in a separate Becher and solubilize it at 65° C.
2. Prepare phase E separately at room temperature.
3. Completely melt phase A in the main Becher at 80° C.—add phase A2.
4. Add phase A3.
5. Emulsification by progressively introducing Phase B in phase A under Rayneri.
6. Dilution by introduction of phase C.
7. Add phase D.
8. Cool the obtained emulsion using a cold water bath.
9. Successively add phases E, F, G at a temperature below 40° C.
10. Add Microcapsules (H) to the emulsion-mixing under Rayneri with propeller blades.

O/W emulsions of examples 1, 2, 3 and 4 are easy to handle and easy to spread on the skin.

These O/W emulsions are not sticky, soft to the touch and their texture is rebounded.

2. Results: Evaluation of the Microcapsules Stability:

The microcapsules stability is characterized by a low rate of non ruptured microcapsules (without applying any rubbing or pressing) in the O/W emulsion bulk after two months at room temperature, 37° C. and 45° C.

This evaluation is performed according to 3 parameters:
number of microcapsules broken in the bulk,
coloration level of the white bulk in beige,
after introduction of a spatula in the bulk: observation of broken microcapsules on the spatula.

|   | Examples 1 and 2 (according to the invention) | Example C (comparative) |
|---|---|---|
| Broken microcapsule number | Not significant | Significant: A lot of broken microcapsule |
| Bulk Coloration | White bulk | Beige bulk |
| Introduction of the spatula | No broken microcapsules | A lot of broken microcapsules on the spatula |

The invention claimed is:

1. A changing colour composition for caring for and/or making up keratin materials in a form of an emulsion, comprising:
   a) releasable colorant comprising microcapsules comprising:
      a core comprising as an organic material at least one monosaccharide-polyol selected from the group consisting of mannitol, erythritol, xylitol, sorbitol and mixtures thereof, wherein the core does not contain a colorant material, and
      a layered coating surrounding said core, the layered coating comprising a polymer and a colorant, and
   b) at least partially neutralized, crosslinked acrylic homopolymer or copolymer, wherein the microcapsules comprise at least two layers of different colors.

2. The changing colour cosmetic composition according to claim 1, wherein the at least partially neutralized, crosslinked acrylic homopolymer or copolymer is a partially neutralized, crosslinked sodium polyacrylate in an inverse emulsion comprising a fatty acid ester.

3. The changing colour cosmetic composition according to claim 1, wherein an oily phase of the emulsion comprises 26% of an oil composed of $C_8$-$C_{10}$ triglycerides.

4. The changing colour cosmetic composition according to claim 1, wherein an amount of the at least partially neutralized, crosslinked acrylic homopolymer or copolymer ranges in terms of active material, from 0.1 to 2.5% by weight, relative to a total weight of the composition.

5. The changing colour cosmetic composition according to claim 1, further comprising a 2-acrylamido-2-methylpropanesulphonic acid polymer.

6. The changing colour cosmetic composition according to claim 5, wherein the 2-acrylamido-2-methylpropanesulropanesulphonic acid polymer is a 2-acrylamido-2-methylpropanesulphonic acid homopolymer.

7. The changing colour cosmetic composition according to claim 6, wherein the homopolymer comprises, distributed randomly, units of formula (I) below:

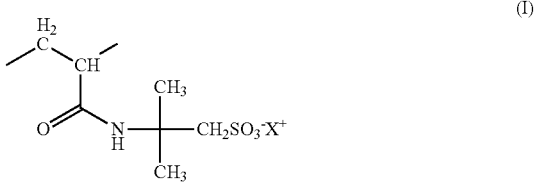

where $X^+$ denotes a proton, an alkali metal cation, an alkaline earth metal cation or an ammonium ion, and a crosslinking unit originating from at least one monomer comprising at least two olefinic double bonds.

8. The changing colour cosmetic composition according to claim 1, wherein the composition is an Oil/Water emulsion, and comprises as stabilizing system, from 0.3 to 0.8%, in terms of active material, of at least neutralized and crosslinked acrylic polymer.

9. The changing colour composition according to claim 1, comprising from 0.1% to 20% by weight of microcapsules relative to a total weight of the said composition.

10. The changing colour composition according to claim 1, wherein the core of the microcapsules comprising a releasable colorant comprises a monosaccharide or a derivatives thereof as said organic material.

11. The changing colour composition according to claim 1, wherein said microcapsules comprises:
an inner core made of monosaccharide-polyol,
at least two layers of different colours, and
a hydrophilic polymer.

12. The changing colour composition according to claim 1, wherein the microcapsules have a size ranging from 10 µm to 800 µm in diameter of the microcapsule and comprise:
a. a core (A) which does not comprise any colorant, and comprises a monosaccharide polyol;
b. one first layer (B) surrounding said core comprising:
   i. a colorant, and
   ii. a binder selected from the group consisting of a polymer, a lipid-based material, and a mixture thereof;
c. one second layer (C) surrounding said first layer (B) comprising:
   i. titanium dioxide particles, and
   ii. a binder selected from the group consisting of a polymer, lipid-based material, and a mixture thereof.

13. The changing colour cosmetic composition according to claim 1, wherein at least one layer of the microcapsules is obtained by fluid bed process.

14. The changing colour cosmetic composition according to claim 1, wherein an aqueous phase comprises at least one polyol selected from the group consisting of glycerol and a glycol.

15. A cosmetic process for caring for and/or making up keratinic materials, the process comprising
applying the changing colour cosmetic composition according to claim 1 on said keratinic materials.

* * * * *